United States Patent [19]

McCartney

[11] Patent Number: 5,778,345
[45] Date of Patent: Jul. 7, 1998

[54] HEALTH DATA PROCESSING SYSTEM

[76] Inventor: Michael J. McCartney, 131 Richmond Street, Richmond Hill, Ontario, Canada, L4C 3Y6

[21] Appl. No.: 586,246

[22] Filed: Jan. 16, 1996

[51] Int. Cl.$^6$ .................................................. G06F 17/60
[52] U.S. Cl. ................................................................ 705/2
[58] Field of Search .................................. 395/201, 202, 395/203; 705/1–3; 283/54, 55; 364/468.05

[56] References Cited

U.S. PATENT DOCUMENTS

| | | |
|---|---|---|
| 3,872,448 | 3/1975 | Mitchell, Jr. . |
| 4,700,295 | 10/1987 | Katsof et al. . |
| 4,722,055 | 1/1988 | Roberts . |
| 4,893,270 | 1/1990 | Beck et al. . |
| 4,957,115 | 9/1990 | Selker .................................. 128/696 |
| 5,018,067 | 5/1991 | Mohlenbrock et al. . |
| 5,301,105 | 4/1994 | Cummings, Jr. . |
| 5,307,262 | 4/1994 | Ertel . |
| 5,319,543 | 6/1994 | Wilhelm . |
| 5,359,509 | 10/1994 | Little et al. . |
| 5,361,202 | 11/1994 | Doue . |
| 5,365,425 | 11/1994 | Torma et al. . |
| 5,557,514 | 9/1996 | Seare et al. .............................. 395/202 |

*Primary Examiner*—Robert A. Weinhardt
*Assistant Examiner*—Frantzy Poinvil
*Attorney, Agent, or Firm*—Barry R. Lipsitz

[57] ABSTRACT

A method and system for evaluating health care provider performance, forecasting health care resource consumption on a macroeconomic scale, and optimizing the allocation of health care resource. The method includes the steps of a) providing patient discharge data which includes an address field indicating one of a plurality of micro-geographical areas (MGAs) wherein a patient resides, b) establishing a referral population for a subject health care provider based upon the market share it has for each cohort in each MGA, c) calculating occurrence rates of medical service demand for the referral population, d) providing and applying population growth factors to the referral population thereby projecting it to a future time, e) applying the occurrence rates to the projected referral population thereby forecasting the consumption of health resources, and f) allocating health care resources in accordance with the forecast. The invention can also factor into the forecast the expected caseload demand from undeveloped or proposed communities. In addition, the invention optionally computes repatriatable caseload volume, i.e. medical service demand which has gone to another health care provider but could be handled by the subject health care provider, and adds this volume to the forecast. Finally, the invention provides for a method for efficiently allocating health resources amongst neighbouring health care providers, based on either current or forecasted medical service demand data.

32 Claims, 14 Drawing Sheets

| M.G.A. | Proportion of usage | Cumulative prop. of usage |
|---|---|---|
| M6A | 35% | 35% |
| M6B | 25% | 60% |
| M6C | 12% | 72% |
| M6E | 8% | 80% ← Pareto efficient point |
| M6L | 7% | 87% |
| M6M | 6% | 93% |
| M6N | 5% | 98% |
| Others | 2% | 100% |

| Referral Population | | | | | | | |
|---|---|---|---|---|---|---|---|
| | AGE GROUP | | | | | | |
| M.G.A. | <-14 | 15-19 | 20-24 | ... | 60-64 | 65-69 | 70-> |
| M6A | 9047 | 5206 | 5486 | ... | 4502 | 3162 | 2951 |
| M6B | 6462 | 3719 | 3919 | ... | 3216 | 2259 | 2108 |
| M6C | 3102 | 1785 | 1881 | ... | 1544 | 1084 | 1012 |
| M6E | 2068 | 1190 | 1254 | ... | 1029 | 723 | 675 |
| M6L | 1809 | 1041 | 1097 | ... | 900 | 632 | 590 |
| M6M | 1551 | 893 | 940 | ... | 772 | 542 | 506 |
| M6N | 1292 | 744 | 784 | ... | 643 | 452 | 422 |
| Others | 517 | 298 | 313 | ... | 257 | 181 | 169 |
| Totals | 25849 | 14875 | 15674 | | 12864 | 9034 | 8432 |

FIG. 6

| Projected Referral Population | | | | | | | |
|---|---|---|---|---|---|---|---|
| | AGE GROUP | | | | | | |
| M.G.A. | <-14 | 15-19 | 20-24 | ... | 60-64 | 65-69 | 70-> |
| M6A | 11547 | 6645 | 7341 | ... | 6315 | 4646 | 4541 |
| M6B | 8248 | 4746 | 5244 | ... | 4511 | 3318 | 3243 |
| M6C | 3959 | 2278 | 2517 | ... | 2165 | 1593 | 1557 |
| M6E | 2639 | 1519 | 1678 | ... | 1443 | 1062 | 1038 |
| M6L | 2309 | 1329 | 1468 | ... | 1263 | 929 | 908 |
| M6M | 1979 | 1139 | 1259 | ... | 1083 | 796 | 778 |
| M6N | 1650 | 949 | 1049 | ... | 902 | 664 | 649 |
| Others | 660 | 380 | 420 | ... | 361 | 265 | 259 |
| Totals | 32991 | 18985 | 20975 | | 18042 | 13274 | 12974 |

FIG. 7

| Dept. | Class Code | Description | Number of Occurrences in Age Group 415 | | | | | | |
|---|---|---|---|---|---|---|---|---|---|
| | | | < - 14 | 15 - 19 | 20 - 24 | ... | 60 - 64 | 65 - 69 | 70 - > |
| Diseases and Disorders of the Circulatory System | 4020 | Malignant Hypertens Heart Dis | 5 | 2 | 3 | | 43 | 78 | 36 |
| | 4021 | Benign Hypertens Heart Dis | 14 | 5 | 5 | | 273 | 573 | 132 |
| | 4029 | Hypertensive Heart Disease Nos | 11 | 11 | 3 | | 474 | 534 | 321 |
| | 4141 | Aneurysm of Heart | 12 | 3 | 4 | | 121 | 234 | 221 |
| | 4151 | Pulmonary Embolism | 4 | 1 | 6 | | 177 | 167 | 246 |
| | 4260 | Antrioventricular Block Complete | 0 | 0 | 1 | | 134 | 175 | 144 |
| | 4261 | Antrioventricular Block Oth/Nos | 0 | 0 | 0 | | 23 | 11 | 25 |
| | 4263 | Other Left Bundle Branch Block | 1 | 0 | 1 | | 24 | 12 | 11 |
| | 4265 | Bundle Branch Block Unspecified | 0 | 0 | 1 | | 23 | 21 | 26 |
| | 4270 | Paroxysml SupraventTachycardia | 2 | 0 | 2 | | 13 | 11 | 9 |
| | 4271 | Paroxysml Vent Tachycardia | 2 | 1 | 1 | | 13 | 31 | 7 |
| | 4272 | Paroxysml Tachycardia Unspecified | 1 | 1 | 0 | | 347 | 384 | 364 |
| | 4273 | Atrial Fibrillation and Flutter | 7 | 5 | 3 | | 363 | 332 | 265 |
| | 4274 | Ventricular Fibrillation and Flutter | 8 | 3 | 3 | | 264 | 322 | 255 |
| | 4275 | Cardiac Arrest | 4 | 0 | 0 | | 251 | 347 | 540 |
| | 4280 | Congestive Heart Failure | 12 | 2 | 1 | | 24 | 15 | 17 |
| | 4281 | Left Heart Failure | 0 | 0 | 0 | | 32 | 21 | 27 |
| | 4289 | Unspecified Heart Failure | 6 | 1 | 0 | | 47 | 34 | 231 |
| | 4295 | Rupture of Chordae Tendinae | 0 | 1 | 1 | | 7 | 11 | 9 |
| | 4296 | Rupture of Papilliary Muscle | 3 | 1 | 0 | | 10 | 14 | 3 |
| | 4298 | Oth Ill-defined Heart Disease | 5 | 4 | 1 | | 34 | 11 | 12 |
| | 4410 | Dissecting Aortic Aneurysm | 1 | 0 | 0 | | 21 | 21 | 14 |
| | 4589 | Unspecified Hypotension | 20 | 10 | 12 | | 1023 | 1231 | 373 |

FIG. 9

| Dept. | Class Code | Description | Occurrence Rate per Age Group | | | | | | |
|---|---|---|---|---|---|---|---|---|---|
| | | | < - 14 | 15 - 19 | 20 - 24 | ... | 60 - 64 | 65 - 69 | 70 - > |
| Diseases and Disorders of the Circulatory System | 4020 | Malignant Hypertens Heart Dis | 0.0193% | 0.0134% | 0.0191% | | 0.3343% | 0.8634% | 0.4269% |
| | 4021 | Benign Hypertens Heart Dis | 0.0542% | 0.0336% | 0.0319% | | 2.1222% | 6.3427% | 1.5655% |
| | 4029 | Hypertensive Heart Disease Nos | 0.0426% | 0.0739% | 0.0191% | | 3.6847% | 5.9110% | 3.8069% |
| | 4141 | Aneurysm of Heart | 0.0464% | 0.0202% | 0.0255% | | 0.9406% | 2.5902% | 2.6210% |
| | 4151 | Pulmonary Embolism | 0.0155% | 0.0067% | 0.0383% | | 1.3759% | 1.8486% | 2.9175% |
| | 4260 | Antrioventricular Block Complete | 0.0000% | 0.0000% | 0.0064% | | 1.0417% | 1.9371% | 1.7078% |
| | 4261 | Antrioventricular Block Oth/Nos | 0.0000% | 0.0000% | 0.0000% | | 0.1788% | 0.1218% | 0.2965% |
| | 4263 | Other Left Bundle Branch Block | 0.0039% | 0.0067% | 0.0064% | | 0.1866% | 0.1328% | 0.1305% |
| | 4265 | Bundle Branch Block Unspecified | 0.0000% | 0.0000% | 0.0064% | | 0.1788% | 0.2325% | 0.3083% |
| | 4270 | Paroxysml SupraventTachycardia | 0.0077% | 0.0000% | 0.0128% | | 0.1011% | 0.1218% | 0.1067% |
| | 4271 | Paroxysml Vent Tachycardia | 0.0077% | 0.0067% | 0.0064% | | 0.1011% | 0.3431% | 0.0830% |
| | 4272 | Paroxysml Tachycardia Unspecified | 0.0039% | 0.0000% | 0.0000% | | 2.6975% | 4.2506% | 4.3169% |
| | 4273 | Atrial Fibrillation and Flutter | 0.0271% | 0.0336% | 0.0191% | | 2.8218% | 3.6750% | 3.1428% |
| | 4274 | Ventricular Fibrillation and Flutter | 0.0309% | 0.0202% | 0.0191% | | 2.0522% | 3.5643% | 3.0242% |
| | 4275 | Cardiac Arrest | 0.0155% | 0.0000% | 0.0000% | | 1.9512% | 3.8410% | 6.4042% |
| | 4280 | Congestive Heart Failure | 0.0464% | 0.0134% | 0.0064% | | 0.1866% | 0.1660% | 0.2016% |
| | 4281 | Left Heart Failure | 0.0000% | 0.0000% | 0.0000% | | 0.2488% | 0.2325% | 0.3202% |
| | 4289 | Unspecified Heart Failure | 0.0232% | 0.0067% | 0.0000% | | 0.3654% | 0.3764% | 2.7369% |
| | 4295 | Rupture of Chordae Tendinae | 0.0000% | 0.0067% | 0.0000% | | 0.0544% | 0.1218% | 0.1067% |
| | 4296 | Rupture of Papilliary Muscle | 0.0116% | 0.0067% | 0.0000% | | 0.0777% | 0.1550% | 0.0356% |
| | 4298 | Oth Ill-defined Heart Disease | 0.0193% | 0.0269% | 0.0064% | | 0.2643% | 0.1218% | 0.1423% |
| | 4410 | Dissecting Aortic Aneurysm | 0.0039% | 0.0000% | 0.0000% | | 0.1632% | 0.2325% | 0.1660% |
| | 4589 | Unspecified Hypotension | 0.0774% | 0.0672% | 0.0766% | | 7.9524% | 13.6263% | 4.4236% |

FIG. 10

| Dept. | Class Code | Description | Expected Number of Occurrences per Age Group | | | | | | |
|---|---|---|---|---|---|---|---|---|---|
| | | | < - 14 | 15 - 19 | 20 - 24 | ... | 60 - 64 | 65 - 69 | 70 - > |
| Diseases and Disorders of the Circulatory System | 4020 | Malignant Hypertens Heart Dis | 6 | 3 | 4 | | 60 | 115 | 55 |
| | 4021 | Benign Hypertens Heart Dis | 18 | 6 | 7 | | 383 | 842 | 203 |
| | 4029 | Hypertensive Heart Disease Nos | 14 | 14 | 4 | | 665 | 785 | 494 |
| | 4141 | Aneurysm of Heart | 15 | 4 | 5 | | 170 | 344 | 340 |
| | 4151 | Pulmonary Embolism | 5 | 1 | 8 | | 248 | 245 | 379 |
| | 4260 | Antrioventricular Block Complete | 0 | 0 | 1 | | 188 | 257 | 222 |
| | 4261 | Antrioventricular Block Oth/Nos | 0 | 0 | 0 | | 32 | 16 | 38 |
| | 4263 | Other Left Bundle Branch Block | 1 | 0 | 1 | | 34 | 18 | 17 |
| | 4265 | Bundle Branch Block Unspecified | 0 | 0 | 1 | | 32 | 31 | 40 |
| | 4270 | Paroxysml SupraventTachycardia | 3 | 0 | 3 | | 18 | 16 | 14 |
| | 4271 | Paroxysml Vent Tachycardia | 3 | 1 | 1 | | 18 | 46 | 11 |
| | 4272 | Paroxysml Tachycardia Unspecified | 1 | 1 | 0 | | 487 | 564 | 560 |
| | 4273 | Atrial Fibrillation and Flutter | 9 | 6 | 4 | | 509 | 488 | 408 |
| | 4274 | Ventricular Fibrillation and Flutter | 10 | 4 | 4 | | 370 | 473 | 392 |
| | 4275 | Cardiac Arrest | 5 | 0 | 0 | | 352 | 510 | 831 |
| | 4280 | Congestive Heart Failure | 15 | 3 | 1 | | 34 | 22 | 26 |
| | 4281 | Left Heart Failure | 0 | 0 | 0 | | 45 | 31 | 42 |
| | 4289 | Unspecified Heart Failure | 8 | 1 | 0 | | 66 | 50 | 355 |
| | 4295 | Rupture of Chordae Tendinae | 0 | 1 | 1 | | 10 | 16 | 14 |
| | 4296 | Rupture of Papilliary Muscle | 4 | 1 | 0 | | 14 | 21 | 5 |
| | 4298 | Oth Ill-defined Heart Disease | 6 | 5 | 1 | | 48 | 16 | 18 |
| | 4410 | Dissecting Aortic Aneurysm | 1 | 0 | 0 | | 29 | 31 | 22 |
| | 4589 | Unspecified Hypotension | 6 | 13 | 16 | | 1435 | 1809 | 574 |

| CMG Range | Major Clinical Category | 1993/94 Day Surgery Cases | 1999 Predicted Day Surgery Cases | Difference (1993-1999) | % Change (1993-1999) | 2004 Predicted Day Surgery Cases | Difference (1993-2004) | % (1993-2004) |
|---|---|---|---|---|---|---|---|---|
| 001-031 | Nervous System | 64 | 71 | 7 | 11.0 | 79 | 15 | 22.8 |
| 050-061 | Ophthalmology | 315 | 373 | 58 | 18.5 | 427 | 112 | 35.6 |
| 075-116 | Otalaryngology | 767 | 808 | 41 | 5.3 | 819 | 52 | 6.8 |
| 124-159 | Respiratory | 26 | 29 | 4 | 13.7 | 34 | 8 | 31.6 |
| 175-222 | Cardiovascular | 27 | 30 | 3 | 10.0 | 32 | 5 | 18.5 |
| 250-331 | Gastrointestinal | 1,390 | 1,545 | 155 | 11.2 | 1,696 | 306 | 22.0 |
| 350-412 | Orthopaedics | 386 | 412 | 26 | 6.7 | 437 | 50 | 13.1 |
| 425-456 | Dermatology/Plastics | 392 | 428 | 36 | 9.1 | 464 | 71 | 18.1 |
| 476-492 | Endocrinology | 8 | 8 | 1 | 8.6 | 8 | 1 | 8.6 |
| 500-538 | Nephrology | 432 | 498 | 66 | 15.3 | 562 | 130 | 30.1 |
| 550-563 | Male Reproductive | 241 | 253 | 12 | 4.8 | 257 | 16 | 6.7 |
| 575-596 | Gynaecology | 1,136 | 1,195 | 59 | 5.2 | 1,256 | 119 | 10.5 |
| 600-613 | Deliveries, etc. | 390 | 393 | 3 | 0.9 | 396 | 6 | 1.5 |
| 625-648 | Neonatal | 0 | 0 | 0 | ERR | 0 | 0 | 0.0 |
| 700-711 | Blood Disease | 23 | 25 | 2 | 8.9 | 27 | 4 | 19.1 |
| 725-738 | Leukaemia/Lymphoma | 37 | 41 | 4 | 11.3 | 45 | 9 | 23.9 |
| 750-763 | Infections | 2 | 2 | 0 | 0.0 | 2 | 0 | 0.0 |
| 770-794 | Psychiatric | 1 | 1 | 0 | 0.0 | 1 | 0 | 0.0 |
| 800-879 | Trauma | 30 | 32 | 1 | 3.8 | 33 | 3 | 8.8 |
| 860-866 | Aids and Aids Related | 0 | 0 | 0 | 0.0 | 0 | 0 | 0.0 |
| 832-999 | Miscellaneous | 307 | 347 | 41 | 13.3 | 386 | 79 | 25.8 |
| | Total | 5,973 | 6,491 | 518 | 8.7 | 6,959 | 986 | 16.5 |

FIG. 12

HEALTH DATA PROCESSING SYSTEM

FIELD OF INVENTION

The invention relates to the field of health data processing systems, and more particularly, to systems which, on a macroeconomic or macroscopic scale, evaluate health care provider performance, forecast health care resource consumption, optimize health care resource allocation, and compute projected health care budgets.

BACKGROUND OF THE INVENTION

The cost of providing health care to our society has mushroomed in recent years, exceeding the capacity of governments and private institutions to adequately finance such cost. Consequently, the budgets allotted to health care facilities of all kinds, both public and private, are under continuous pressure in this era of fiscal restraint. In an effort to provide adequate service to the public yet conserve financial resources, it is highly desirable to optimize the allocation of health resources, which includes infrastructure, physical equipment and manpower, so that these resources are used to maximum efficiency.

There are a number of problems in attempting to optimize the allocation of health resources. In examining a particular health care provider, it is first necessary to quantify efficiency and capacity utilization to determine whether these levels are at acceptable levels, thereby identifying surplus resources.

There are also problems in attempting to optimize the allocation of health resources amongst a group of health care providers. For example, in a political jurisdiction or geographic boundary, there are often a number of health care providers, each of which may offer substantially similar services. It is unclear how to identify service redundancies amongst the various health care providers, bearing in mind that they may primarily attract clients from various locales, each of which requires some minimal level of medical service. In addition, there is the problem of determining an efficient geographical scope for a health care provider. This will depend upon the composition of a referral population associated with the health care provider, which leads to the issue of how to identify or distinguish the referral population from the general population in the jurisdiction.

Assuming that operating deficiencies and overcapacities can be identified, there still remains the problem of distributing health care resources. Health care resources are typically massive, involving the complex inter-relationships of physical facilities, infrastructure, costly equipment, and specialized, often scarce personnel. These assets are not readily relocatable, hence any health resource rebalancement must take into account not only the present demand but also the future demand on these resources, in at least a five to ten year time frame. Thus, it would be beneficial to the budgeting and optimization process to be able to forecast the future demand on health resources.

There are a number of problems in attempting to forecast the consumption of health care resources. One of the problems, as mentioned above, is identifying the referral population for a particular health care provider. This is important because referral populations associated with various health care providers can have significantly differing demographic characteristics which demand differing levels of medical service. A related problem is determining an appropriate population growth factor for the referral population (which occupies specific locales in a jurisdiction) as this growth rate may be significantly different than published growth rates for the general population of the jurisdiction. It should be appreciated that the growth rate(s) for the referral population will have a significant effect upon the health care resource forecast.

One system, disclosed in U.S. Pat. No. 5,018,067, issued May 21, 1991, to Mohlenbrock, and entitled Apparatus and Method for Improved Estimation of Health Resource Consumption through use of Diagnostic and/or Procedure Grouping and Severity of Illness Indicators, attempts to estimate the resource consumption, e.g. in terms of cost or length of stay, for a given patient. This system works in conjunction with public domain software for determining the appropriate Diagnostic Related Group ("DRG") category based on underlying International Classification of Disease ("ICD") codes typically used to classify diseases and procedures therefor in the typical patient composite file that a health care facility compiles during the patient's stay or visit to the facility.

(The DRG system is a United States federally mandated system for setting the amount of payment that a hospital or other type of health care provider will receive from the U.S. federal government for that patient under the Medicare reimbursement system. Under this system, termed a prospective payment system, the amount of payment per patient is determined by the type of disease(s) the patient is categorized with and/or the medical procedures performed thereon. There are hundreds of DRG categories, and once the patient is slotted into one DRG group, the hospital is paid a set amount irrespective of the actual cost to the hospital of treating the patient.

There are many more distinct types of medical cases than DRG groups, so federal regulations decree how a patient, who often exhibits a number of maladies, is categorized under the DRG system. These regulations have been codified into programs, known as DRG grouper programs, which select the appropriate DRG class based upon the underlying disease manifestations and medical services performed in respect thereof. The DRG grouper program operates on the basis of the ICD coding system developed by the World Health organization. The latter is a coding system widely used by health care facilities in North America for the classification of diseases, injuries, symptoms, impairments, medical procedures and causes of death. It is much more detailed than the DRG system, having about 15,000 categories, and it is usually compiled as part of a patient's treatment record at the health care facility. Structurally, the ICD system is initially divided into Disease and Procedure sections, and each of these is further divided into numerous categories and sub-categories further defining disease manifestations and/or diagnostic procedures. The current version of the ICD coding system is termed ICD-9-CM, meaning the 9th revision, Clinical Modification of the original ICD system. Further information about the DRG system and its relationship with the ICD system can be found in the Mohlenbrock reference, all of which is incorporated herein by reference.)

The DRG system establishes government decreed benchmarks for resource allocation for particular diagnoses and/or surgical procedures. However, since a patient can have many illnesses and/or surgical procedures performed all at once, and since the DRG classification system generally only reflects the primary illness or surgical procedure for cost recovery purposes, application of the DRG classification system to resource utilization estimation for a particular patient (once the patient is completely diagnosed) can result in a wide variance from the mean. Viewed another way, the hospital population group falling under a particular DRG class is not a very homogeneous mix thereby resulting in a large variance of the mean cost recovery for a given patient.

In order to overcome this problem, the Mohlenbrock system attempts to calculate the severity of illness for a given patient in order to better estimate resource consumption. It does this by means of an acuity index for each DRG class. By categorizing the given patient as to how acute his affliction is within the DRG class, it is hoped that there is a much more homogenous statistical population by which to estimate resource consumption. This estimate is calculated by factoring the standard cost recovery amount associated with the DRG class in accordance with the acuity index in order to obtain a better estimate of resource consumption. The level of factoring is based upon actual historical data for said DRG class.

The Mohlenbrock system quite clearly has a microeconomic focus; that is, it attempts to predict the cost for treating a given patient once that patient has been properly diagnosed. There is a need, however, for a system having a macroeconomic focus which attempts to forecast the cost or caseload for the health care provider as a whole, considering all of its clients, and to project the health care provider's budget or resource needs a number of years into the future. Additionally, there is a need for a system which can identify service redundancies or overcapacities between health care providers within a given region and suggest ways in which health resources can be optimally allocated. The present invention seeks to accomplish these objectives and is useful to health care service administrators, health care planners, insurers and others who wish to determine the optimal way to meet challenges in the future.

LEXICON

| | |
|---|---|
| health care provider | A general term for any institution or facility providing medical services and treatment. Private health practitioners, such as small physicians' offices, however, are not contemplated in the definition. |
| Diagnosis | A categorization of the type(s) of disease manifestation a patient is afflicted with, or alternatively, the service(s) of diagnosing the disease manifestation. |
| Medical Procedure | Any diagnostic or surgical procedure such as X-ray scanning, open heart surgery, etc. |
| Medical or Health Provisions | Consumable supplies furnished by the a health care provider to its patients, and including items such as drugs, disposable medical equipment such as needles, food, etc. |
| medical services | Includes all Diagnoses and Medical Procedures. |
| health resources | A generalized term including medical services, Medical Provisions, health care provider manpower resources as well as medical equipment and infrastructure. |
| Patient Record | An exhaustive record compiled during a patient's visit or stay at a health care provider detailing the patient's characteristics, such as age, sex, address, financial information etc., relevant Diagnoses, Medical Procedures and Medical Provisions provided thereto, as well as the patient's utilization of other resources. Most jurisdictions require the compilation of this type of information, and typically the health care provider employs the ICD-9 coding system in compiling the Patient Record. |

-continued

| | |
|---|---|
| International Classification of Diseases-9th revision, Clinical Modification (ICD-9) | A coding system widely used by health care providers in North America for the classification of disease manifestations, injuries, symptoms, impairments, (i.e. Diagnoses), Medical Procedures and causes of death. The ICD-9 coding system specifies about 15,000 various categories, and it is usually used in the Patient Record. Structurally, the ICD-9 system is initially divided into Disease and Procedure sections, and each of these is further divided in numerous categories and sub-categories further defining disease manifestations and/or medical procedures. |
| Case Management Group (CMG) or Diagnostic Related Group (DRG) | Classification system which group the many primary classification codes such as the ICD-9 codes into related medical service groups. The DRG are employed mainly in the United States for the purposes of prospective payment systems whereas the CMG is employed primarily in Canada. ("CMG" is a trademark of the Canadian Institute of Health Information, Toronto, Ontario). The two systems are similar, although not identical. |
| Department | An occupational unit within a health care provider, such as Obstetrics, Ultrasound, Orthopaedics, etc. A department is associated with a plurality of underlying Diagnoses and Medical Procedures (typically as represented by the ICD-9 coding system), i.e. there exists a one-to-many relationship therebetween. |
| patient population | The actual collection of patients serviced by a given health care provider within a specified time frame. |
| Boundary Region | The total geographical area under analytical consideration. This is a user supplied input to the system and depends very much on the type of health care provider(s) being analyzed. For example, if the Mayo Clinic is being considered, then the Boundary Region would likely be the north-eastern United States. If a typical city hospital is under consideration, then the entire city would likely be the Boundary Region. |
| Micro-geographical Areas (MGAs) | Sub-area(s) within the Boundary Region which have roughly equal numbers of residents. Preferably, the MGAs are defined in terms of zip codes or postal codes, but other kinds of addressing information can also be employed. The size of the MGA varies depending upon the specific application of the system. For example, if the Boundary Region is the north-eastern United States, then one could use counties therein as the MGAs. As another example, if the Boundary Region is the City of Toronto, one could use postal codes (or forward sorting areas-the first 3 digits of the postal code) to define the Micro-geographical Areas. |
| Catchment Area | A set of Micro-geographical Areas within the Boundary Region, the residents of which account for the bulk of a health care provider's clients. More particularly, the set composes a group of MGAs wherein the residents thereof have the highest utilization rate of the subject health care provider, the group being limited |

| | |
|---|---|
| | to a cumulative, specified utilization of the health care provider under consideration. Under such a condition the set is said to be Pareto efficient. The catchment area can be established with respect to all services provided by a given health care provider or for specific medical services provided thereby. |
| Referral Population | A portion of the general population which can be considered to be the population which looks primarily to a given health care provider for their health needs. The referral population can be established with respect to all services provided by a given health care provider or only for specific medical services provided thereby. |
| Projected Referral Population | A Referral Population projected into the future. Typically, the Referral Population will grow due to general population growth. |
| Occurrence Rate | A computation representing the rate at which a given type or category of medical service is required by a specified population or cohort thereof. This computation is related to the rate of disease manifestation in the population. |
| Isarythmic Boundary | A boundary demarking an area wherein all the residents thereof are geographically closer to a specified health care provider than any other health care provider, of the same or dissimilar type. |
| Community, Regional and Teaching Hospitals | Hospitals which provide medical services of varying scope. Teaching hospitals, which are usually affiliated with universities, provide all medical services in substantially all specialities. Regional hospitals typically handle a wide variety of medical cases, but tend to not handle particularly complex cases nor is every type of medical speciality available. Community hospitals are categorized by a significantly restricted level of medical services available to the public. |

SUMMARY OF INVENTION

The health data processing system of the invention provides a number of macroeconomic analyses. The system functionality includes:

(a) determining, by a technical method, a statistically significant geographical area, i.e. a Catchment Area, serviced by a health care provider or group thereof for one or more types of medical service and the mapping thereof;

(b) determining the catchment areas for two or more health care providers and for one or more types of medical service and comparing them for service redundancies, thereby providing a tool for the rebalancing of health resources within a geographic area;

(c) identifying the specific demographic characteristics of a portion of the general population which looks primarily to one or more given health care providers for their health needs, i.e. determining a Referral Population for the subject health care provider(s);

(d) accurately forecasting the future demand on health resources for the subject health care provider(s) and future budget therefor based on a projection of current cost or based upon a prospective payment system;

(e) projecting the effect of new, proposed communities on the health resource demand forecast;

(f) comparing the performance of the subject health care provider(s) with other health care providers, identifying potential areas for improvement, and calculating projected budgets assuming said improvements are employed; and (g) determining the patient repatriation potential for the subject health care provider(s) in terms of potentially capturable market share.

According to one aspect of the invention, there is provided a computer-implemented method of optimizing the allocation of health resources for at least one subject health care provider by forecasting future demand for medical services. The steps of this method include: 1) providing census data and patient discharge records for substantially all of the patient populations of the subject health care provider and other major health care providers within a boundary region, wherein the patient discharge record includes an address field which indicates one of a plurality of micro-geographical areas (MGAs) where a patient resides, the MGAs for logically apportioning the boundary region into sub-areas having roughly equal population sizes; 2) establishing a referral population, which preferably includes the steps of identifying the demographic characteristics of the population residing in the boundary region, determining the market share of the subject health care provider in the boundary region, and selecting portions of the total population of the boundary region generally in accordance with the market share to thereby establish the referral population; 3) calculating occurrence rates of medical services for the referral population; 4) providing and applying population growth factors to the referral population thereby projecting it to a future time; 5) applying the occurrence rates to the projected referral population thereby forecasting the consumption of health resources for the subject health care provider; and 6) altering the composition of the health care provider's resources in accordance with the forecast.

Preferably, the population of each unique MGA (listed in the patient discharge data) is segmented into a specified number of age and sex cohorts, and the step of determining a referral population further includes the steps of: a) determining a current population size, $S^o_{coh,mga}$, per cohort, per MGA; b) determining a number, $N_{coh,mga}$, of people attending any health care provider, per cohort, per MGA; c) determining a number, $H_{coh,mga}$, of people attending the subject health care provider, per cohort, per MGA; and setting a referral population size, $R^o_{coh,mga}$, for a given cohort and a given MGA, such that $R^o_{coh,mga} = S^o_{coh,mga} * (H_{coh,mga}/N_{coh,mga})$.

In addition, the step of projecting the referral population preferably includes the steps of: computing a projected population size, $S^t_{coh,mga}$, per cohort, per MGA, by applying the growth factors to $S^o_{coh,mga}$, and computing a projected referral population size, $R^t_{coh,mga}$, per cohort, per MGA, where $R^t_{coh,mga} = S^t_{coh,mga} * (H_{coh,mga}/N_{coh,mga})$.

Furthermore, the occurrence rates can be calculated as static rates or can be in the form of a regression equation derived from historical occurrence rate data. In either case, the occurrence rates are preferably computed in respect of ICD-9 codes found in the patient discharge records.

In the preferred embodiment, the population growth factors are computed for a given MGA by employing published growth factors for a political jurisdiction associated with the given MGA and varying the published figure generally in accordance with the number of housing units planned therefor. Where the number of housing units are greater than a threshold value, such as the mean number of planned housing units for the MGAs composing the jurisdiction, the growth factor employed in respect of the given MGA is adjusted upward. Conversely, where the number of planned housing units is lower than the threshold value, the growth factor employed in respect of the given MGA is adjusted downward.

According to another aspect, the inventive method includes the steps of: providing housing development planning data for a proposed community; establishing the demographics of the proposed community in accordance with historical data in respect of past housing developments which occurred in an MGA wherein the proposed community is situated; estimating a number of occurrences of medical services for the proposed community in accordance with occurrence rates derived from a general population; and incorporating the estimated number of medical service occurrences with the amount of medical services occurrences calculated for the MGA the proposed community is located in.

The preferred embodiment also includes the step of computing a financial budget for the subject health care provider, which computation may be based on a prospective payment system or as a projection of current cost.

According to another aspect of the invention, there is provided a computer-implemented process for optimizing the allocation of health care resources amongst a plurality of health care providers situated within a boundary region, comprising the steps of: 1) providing a patient record composite file (PRCF) having patient records for substantially all of the subject health care provider's patient population and other major health care providers within the boundary region, wherein the patient record includes an address field indicating one of a plurality micro-geographical areas (MGAs) where a patient resides, the MGAs for logically apportioning the boundary region into sub-areas having roughly equal population sizes; 2) establishing a catchment area for each health care provider; 3) comparing the geographic scope of the catchment areas; 4) computing for each health care provider a patient/physician ratio for at least one category of medical service; and 5) providing the catchment areas at least partially overlap, redistributing or altering the health resources associated with the health care providers in accordance with the patient/physician ratios. The catchment area is preferably established by determining, for each health care provider, the number of patient discharges per unique MGA, and then selecting a subset of MGAs having the highest levels of patient discharges such that the subset composes a Pareto efficient geographic distribution of the health care provider's patient population.

According to yet another aspect of the invention, there is provided a computer-implemented process for optimizing the allocation of health care resources of at least one subject health care provider. The process includes the steps of: 1) providing a patient record composite file (PRCF) having patient records for substantially all of the patient populations of the subject health care provider and other major health care providers within a boundary region, wherein the patient record includes an address field which indicates one of a plurality micro-geographical areas (MGAs) where a patient resides, the MGAs for logically apportioning the boundary region into sub-areas having roughly equal population sizes; 2) establishing a catchment area for the health care provider; 3) selecting, from the PRCF, patient records in respect of patients seeking health services outside of the catchment area, thereby forming a set; 4) calculating an isarythmic boundary for the subject health care provider; 5) excluding from the set patient records in respect of patients living external to the isarythmic boundary; 6) excluding from the set patient records in respect of complex cases transferred to specified health care providers; and 7) altering the composition of health resources for the subject health care provider in accordance with categories of medical service listed in the set.

BRIEF DESCRIPTION OF THE DRAWINGS

The invention will be more fully understood with reference to the following detailed description and accompanying drawings, wherein:

FIG. 6 is a schematic illustration of an electronic data table representing a Referral Population;

FIG. 7 is a schematic illustration of an electronic data table representing a Projected Referral Population;

FIG. 9 is a schematic illustration of a portion of an electronic data table representing current case loads for a Referral Population;

FIG. 10 is a schematic illustration of a portion of a data table representing current Occurrence Rates for the Referral Population;

FIG. 11 is a schematic illustration of a portion of data table representing projected case loads for a Projected Referral Population;

FIG. 12 is an example of a case load forecast report;

DETAILED DESCRIPTION OF PREFERRED EMBODIMENTS

The health data processing system of the invention comprises a hardware element 10 and a software element 25.

Figure 1:
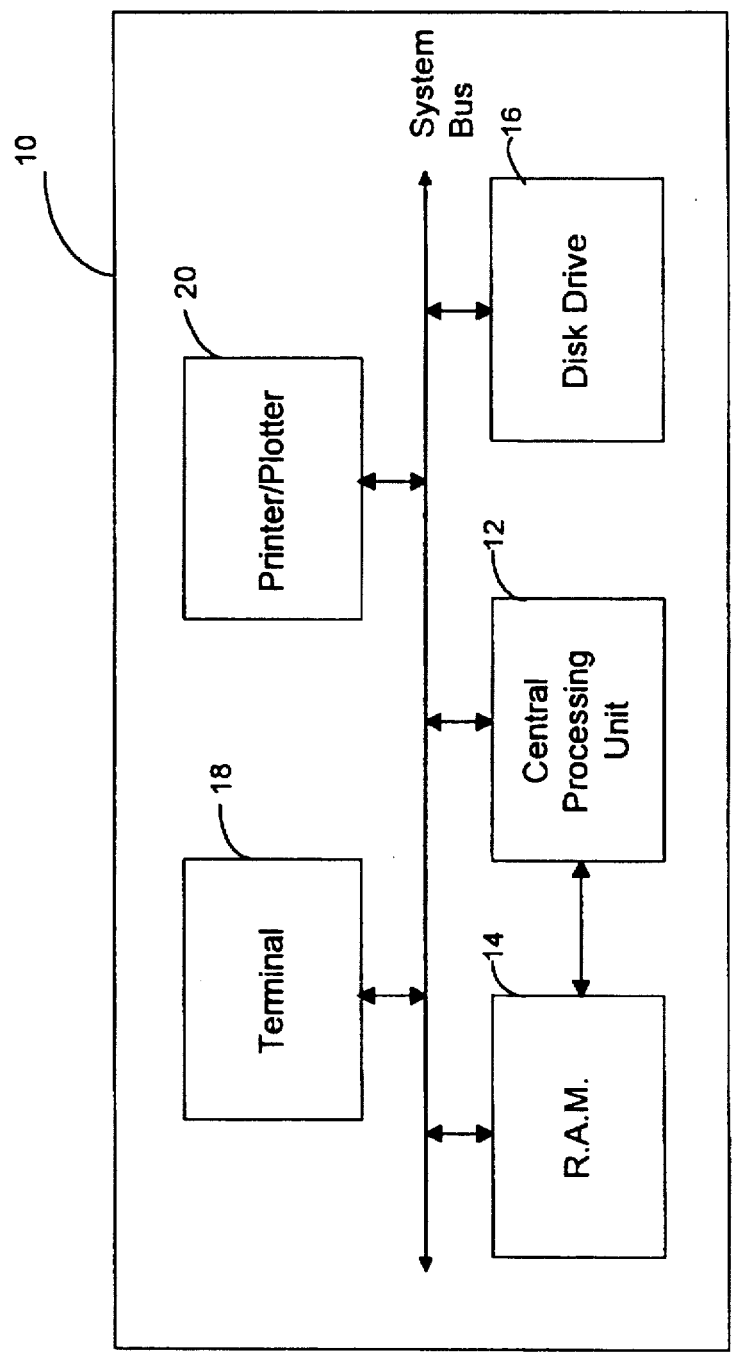
FIG. 1 is a block diagram of a conventional computer system for operating the health data processing system (hereinafter "system") of the invention.

FIG. 1 shows, in block diagram form, the hardware element 10 which is a typical digital computer system comprising a central processing unit 12, a random access memory 14, an alterable, non-volatile secondary storage means such as a disk drive 16, and input-output means such as a terminal 18 and a printer 20. Practically any general purpose digital computer can be used for the hardware element of the invention, and as this is a common component of most data processing systems, it shall not be discussed further.

Figure 2:
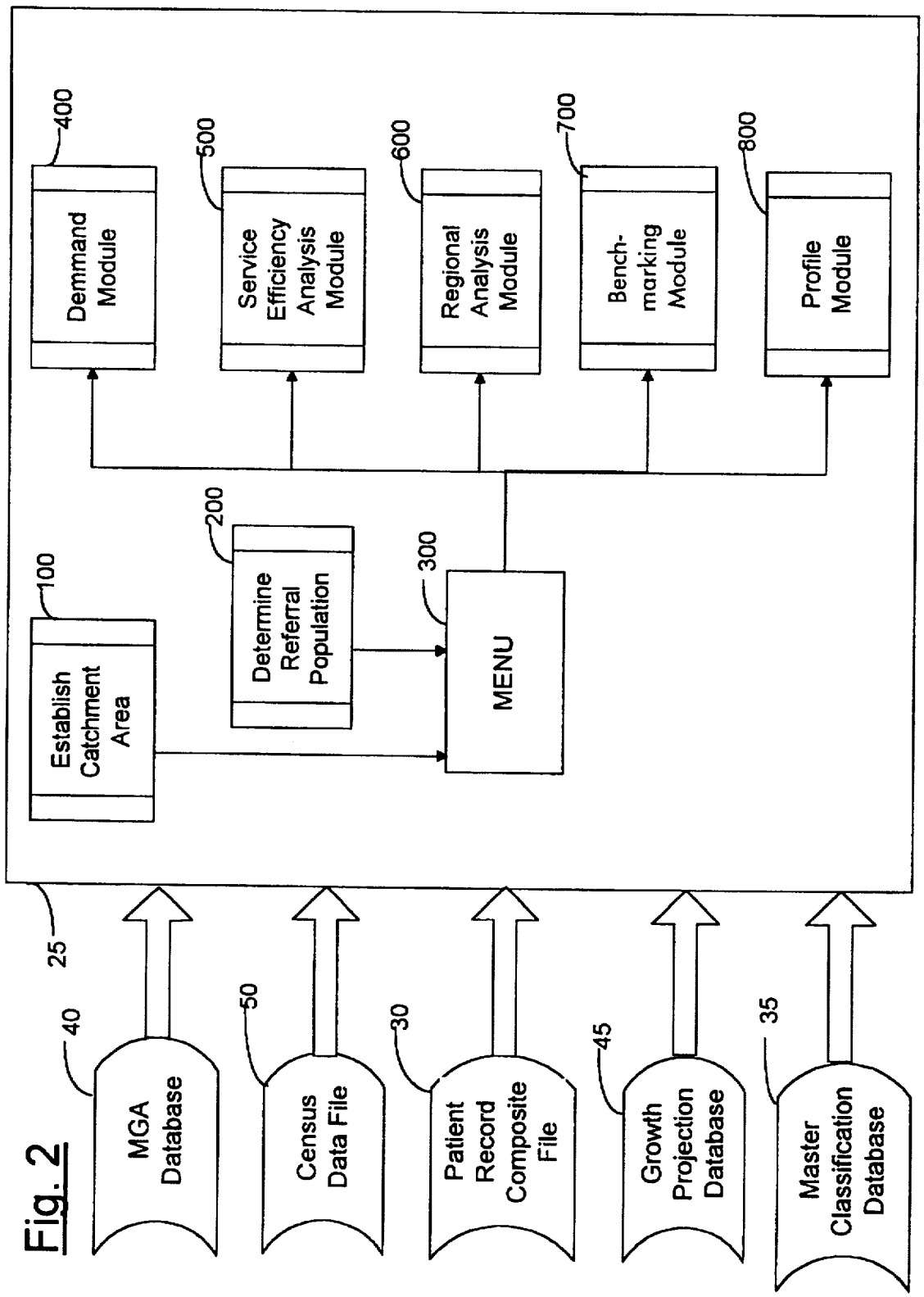
FIG. 2 is a block diagram illustrating major software modules of the system according to a preferred embodiment of the invention.

FIG. 2 shows the main software modules of the system 10 and some of the data files which the system utilizes. In order to provide the proper backdrop by which to explain the operation of the software 25, the data files shown in FIG. 2, along with related terminology, are first discussed.

Data Files

Patient Record Composite Data File 30 (hereinafter alternatively "PRCF") is a data file which preferably contains, in computerized or digitized form, substantially all of the Patient Records for one or more health care providers situated within a defined area. The Patient Record, as mentioned above, is compiled during a patient's visit or stay with a health care provider and is a record of the particulars thereof, such as patient name, address, sex, age, insurance number and other financial status as well as a record of the patient's Diagnoses, Medical Procedures and Provisions supplied by the health care provider to the patient. The vast majority of health care providers in North America employ the known ICD-9 coding system, as described earlier, for coding the Diagnoses and Medical Procedures listed in the Patient Record, and the preferred embodiment of the software 25 anticipates the use of this coding system in the PRCF 30. However, alternative coding systems, such as the known Diagnostic Related Groupings (DRG) or Case Mix Groupings (CMG) can be used as the classification system for the PRCF 30. In any event, the PRCF 30 preferably includes Patient Records compiled or accumulated by the health care provider(s) for at least a one year time frame, and most preferably for many contiguous years.

Master Classification Database System 35 (hereinafter alternatively "MCD") is a database which associates the classification system used in the PRCF 30, termed the primary classification system, with one or more secondary or hierarchical classification systems. It should be appreciated that the primary classification system, such as the preferred ICD-9 coding system, is a very detailed categorization scheme and hence it is difficult to communicate macroeconomic information to persons based on this system. For example, it would be difficult for a person to comprehend the overall impact of a forecasted change in case load per each ICD-9 incident over time, so a higher level classification system is necessary in order for persons to readily digest such information. In the preferred embodiment, a three tiered hierarchical classification structure is employed. At the lowest or primary level, the ICD-9 coding system is used and it is featured in the Patient Record and corresponding PRCF 30. At a secondary or intermediate level, the DRG or CMG classification scheme or a customized classification, as the case may be, is employed to group the great number of ICD-9 classes into far fewer DRG categories. Finally, at the tertiary or top most level, the DRG groupings and ICD-9 codes are linked to major clinical categories or specified organizational units within a health care provider's organizational structure, i.e. Departments associated with major clinical categories. (A typical hospital, as one example of a general care health care provider, is organized into approximately 14 programs or departments, each dealing primarily with one major clinical category or body system, such as cardiovascular, gastrointestinal, neonatal, blood diseases etc.) Each Department has a plurality of DRG groupings and ICD-9 classifications associated therewith. The uses of these classification hierarchies will become more apparent as the software 25 is described in greater detail below, but in general, the primary classification scheme is used for data processing purposes while the highest level classification scheme is employed for reporting purposes.

It should be appreciated that in the preferred embodiment the MCD 35 is not simply a passive database having pointers linking the codes of the three classification schemes together but, because of the use of the DRG classification system, is rather an "active" database or rule-based system employing logic, such as the prior art DRG grouper software, to determine the association between the ICD-9 codes listed in a Patient Record with one DRG code. In alternative embodiments, the master classification database system can be based on a bi-level structure, having, for example, only a Department-DRG category relationship (i.e. where the Patient Record is based upon the DRG grouping) or only a Department-ICD-9 class relationship, and in these cases a simpler pointer-linked database structure can be employed. One diagnosis may therefore be part of two programs.

Micro-geographical Area Database 40 (hereinafter alternatively "MGAD") includes a listing of relatively small geographical regions, termed Micro-geographical Areas (MGAs), which preferably have approximately the same number of people residing therein. The MGAs are preferably represented or codified by employing postal addresses or portions thereof, such as a United States zip code or the forward sorting area (FSA), i.e. the first 3 digits, of a Canadian postal code. Advantageously, the zip or postal code scheme has been set up so that each unique code thereof represents an area roughly equal in population size. In addition, depending upon the area being studied, other geographical data can be employed for the MGAD, such as towns, counties, census areas and residence codes. In any event, the MGAD is used to apportion a large region into smaller areas for data processing purposes.

The MGAD 40 can usually be obtained from the postal authorities of a jurisdiction. Alternatively, the MGAD 40 can be compiled from the PRCF 30 by identifying all unique instances of the zip code or FSA from an address field of the Patient Record. In alternative embodiments, the MGAD 40 can employ geographical co-ordinates for codifying the MGAs, but this is not as convenient as using the postal codes because in the latter case there is no need to translate or link postal codes listed in the Patient Record into geographical co-ordinates.

Census data file 45 is a data file comprising the typical census data which is commissioned by government agencies every few years and designed to accumulate information concerning the characteristics, i.e. demographics, of the populace in a political jurisdiction. It includes records having fields representing the names and ages of all family members in one household, the household address, household income(s), occupation(s), possibly the dominant ethnicity or religion of the household and mother tongue, and various other particulars depending upon the jurisdiction in which the census was taken. The census data file is usually publicly available for purchase from the government department which commissioned the census, typically a Statistics department.

Population growth projection database 50 includes records which associates each MGA with a population growth factor. These growth factors are preferably obtained from government Statistics departments, and are computed based on birth, death, migration and immigration rates. The growth factors may not be initially cast in terms of the growth factor per MGA, but will typically be a growth factor for a larger region, such as a whole municipality, so the population growth data file may have to be specifically prepared for use with the software 25, as is described in greater detail below. In addition, in the preferred embodiment database 50 also includes records in respect of present and historical municipal planning data, such as the locations and number of proposed housing units to be constructed and the price ranges thereof. The system uses this data in conjunction with the government supplied population growth factors to more accurately assess population growth in the MGAs, as described in greater detail below.

System Overview

One of the precursor or initialization tasks of the software 25 is to determine a statistically significant geographical area, i.e. a Catchment Area, serviced by a health care provider or group thereof within a larger Boundary Region. This function, which is used by some of the other modules in the system, generates a visual map of the statistically significant geographic area serviced by a health care provider.

The above function is implemented by a program module or procedure 100 which employs a technical method for determining the statistically significant sub-areas serviced by one or more given health care providers (or at least one type of Department thereof) throughout the Boundary Region. The Catchment Area is identified as a set of MGAs wherein a portion of the residents thereof compose a majority of the patient population of the health care provider under consideration, as described in greater detail below. One advantage of employing the present method for determining Catchment Areas is that it is possible to compare the levels of service supplied by similar Departments of various health care providers within the Boundary Region. Accordingly, it is possible to identify service redundancies between the health care providers in the Boundary Region and hence optimize the allocation of health resources therein. This latter function is provided by a service efficiency analysis module 500.

Another program module or procedure 200 determines a Referral Population (and its associated demographics) for a health care provider or group thereof under consideration (hereinafter alternatively termed "subject health care provider", the singular form also including cases where a group of health care providers is under consideration). The Referral Population is selected from the general or total population residing in the Boundary Region, and reflects the market share of the subject health care provider in comparison with other health care providers situated in the Boundary region. (The "market" is defined as the portion of the general population requiring any type of medical services from the major health care providers in the boundary region.) The assessment of the Referral Population demographics is important in order to ensure accurate forecasts of future health resource demand, it being appreciated that various health care providers within the Boundary Region might have associated referral populations possessing considerably different demographics which can "grow" differently. Module 200 also calculates a Projected Referral Population, i.e. the Referral Population projected into the future, based on the population growth factors contained in growth projection database 45.

A menu module or procedure 300 provides a user interface menu for enabling a user to choose among a number of additional modules, most of which utilize the assessments of the Catchment Area and Referral Population described above.

A demand module or procedure 400 forecasts the future demand on health resources for the subject health care provider and future budget therefor based on a projection of current cost or on a prospective payment system. This module operates by determining Occurrence Rates for disease manifestations and medical procedures therefor (as codified by the ICD-9 codes) in the Referral Population and then applying the Occurrence Rates with respect to the Projected Referral Population. The results are preferably reported as an expected number of caseloads per Department or increase thereof.

A regional analysis module or procedure 600 determines the patient repatriation potential for the subject health care provider in terms of capturable patient market share, i.e. the number of patients frequenting health care providers other than the subject provider within the Boundary Region. Module 600 preferably operates by considering only that portion of the Referral Population which is situated geographically closer to the subject health care provider than any other health care provider, i.e. within an Isarythmic boundary. Module 600 preferably provides reports listing the repatriation potential by Department for medical services currently being provided by the subject health care provider as well as services which it does not currently provide.

A benchmark module or procedure 700 computes efficiency indicators, such as average length of stay (ALOS), ratio of day surgery to non-day surgery cases, etc., for one or more types of medical service. These indicators are compared against benchmark values to identify areas where the subject health care provider is inefficient.

A profile module or procedure 800 analyzes the impact of proposed new communities upon the forecasted health resource demand for the subject health care provider. In many municipalities or political jurisdictions, such as the typical North American suburb of a large city, the population is growing at a fast pace. Typically, the plans for new housing projects or subdivisions are approved by the relevant zoning or planning authorities a few years before the actual construction and completion of the subdivisions. However, at the time the subject health care provider is analyzed, there is little or no representative data in the PRCF 30 which reflects the health resource consumption needs of the proposed subdivisions or communities. Module 800 assesses the impact of the proposed communities on the health demand forecast. It does this by querying for the amount of expected housing units and the price ranges thereof for the proposed communities. From this, and historical information, it is possible to predict the statistical composition of the residents of the proposed communities, i.e. the number of people composing the family, their ages, etc.. Given this proposed population and the demographics thereof, it possible to estimate the future Occurrence Rates of disease manifestation and associated medical procedures for the proposed communities and include these in the health resource demand forecast. This module is particularly useful for improving the accuracy of the health demand forecast at the micro-geographical level thereby allowing a health provider to predict the potential impact of certain large developments.

The discussion now turns towards describing each of modules 100–800 in greater detail.

Establishing Catchment Area

Figure 3:
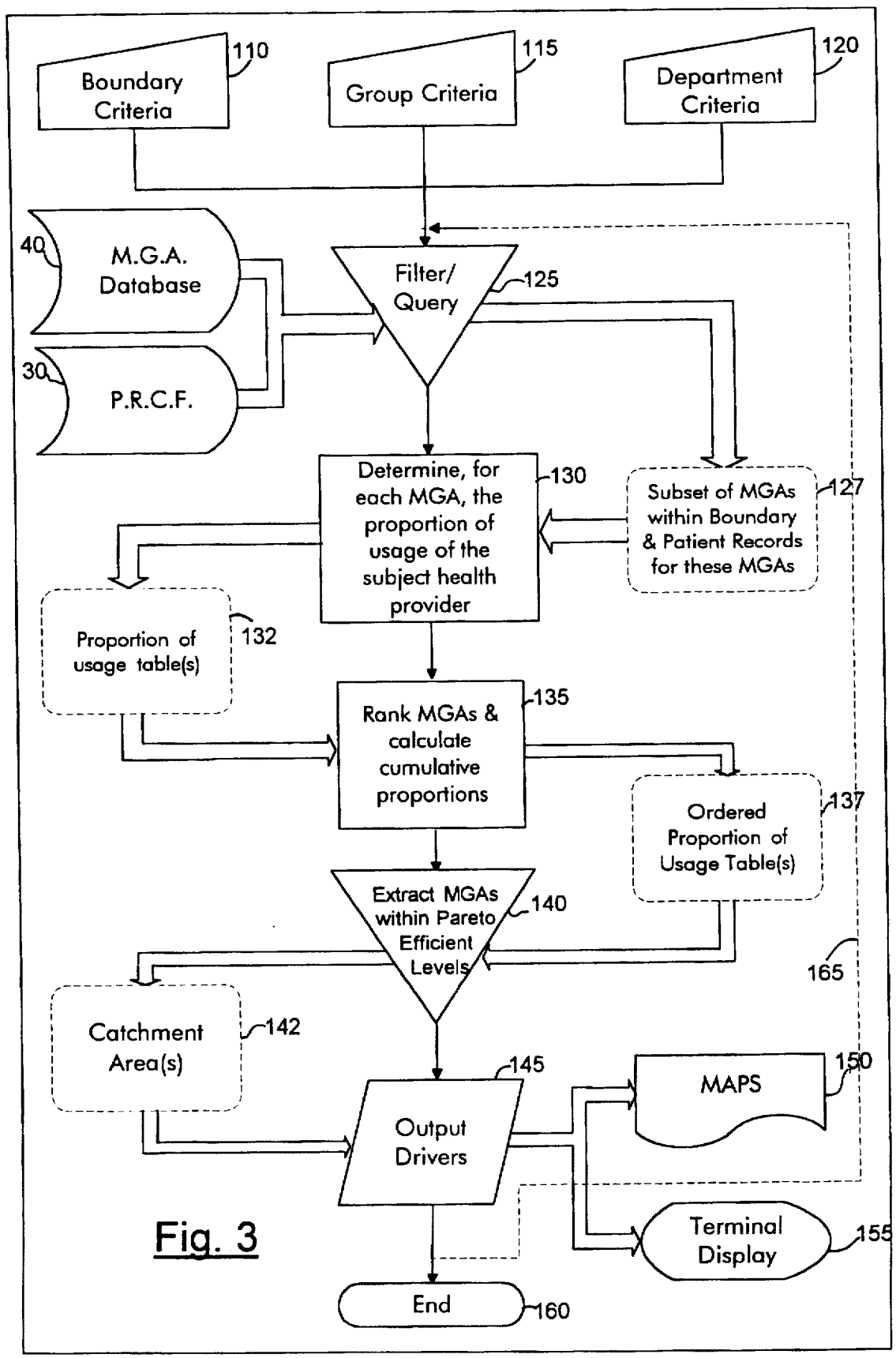
FIG. 3 is a flow diagram of a module which determines a Catchment Area.

FIG. 3 illustrates the procedural or instructional sequence and data flow of module 100, which establishes a Catchment Area. Initial steps 110, 115 and 120 accept user25 supplied criteria for database filtering or querying purposes, and step 125 queries or filters the PRCF 30 and MGAD 40 based upon the criteria.

Step 110 accepts parameters for a Boundary Region, which defines the overall geographic scope for the analysis of the PRCF 30 and the determination of the Catchment Area. This is necessary because the PRCF 30, particularly if it is obtained from a commercial source, may contain the Patient Records from all health care providers for a very large area, such as a state or province, whereas it is only desired to consider a subject health care provider with reference to a smaller area, such as city, for example. The scope of the Boundary Region is usually suggested by the type of health care provider to be analyzed. For Regional Hospitals, the immediately surrounding municipalities can typically be considered to be the relevant Boundary Regions, whereas for Teaching Hospitals, such as the Mayo Clinic, for example, one could consider the state of Minnesota and even the entire north-eastern United States as the relevant Boundary Region.

The Boundary Region parameters are preferably defined and accepted by the system in accordance with the type of data used to delimit the MGAs in the MGAD 40. Hence, if the FSA of postal codes or zip codes are used in the MGAD 40, then the Boundary Region parameters can simply be preferably a comprehensive list thereof or a list of the MGAs forming the outer perimeter of the Boundary Region.

Step 115 accepts information relating to which health care provider or group thereof in the Boundary Region are to be considered as the subject health care provider.

Step 120 accepts input concerning which specific Departments are to be considered in determining the Catchment Area.

A second step 125 is a data querying or filtering step. It utilizes the criteria obtained in input steps 110, 115, and 120 to query or filter the MGAD 40, as is known in the art of database programming, so that only a subset of MGAs situated within the Boundary Region are returned (by a query instruction) or are viewable or otherwise accessible from the MGAD 40 (as a result of a filtering instruction), as shown by a data set or array 127. Step 125 also queries or filters the PRCF 30, as is known in the art, such that only those Patient Records that match the criteria set by steps 115 and 120 are returned or accessible, as the case may be. In alternative embodiments, the PRCF 30 can be grouped by MGA, thereby enabling each unique instance of MGA to be determined and avoiding recourse to a master list of MGAs.

A third step 130 determines, for each MGA listed in data set 127, the proportion of usage of the subject health care provider, or given Department thereof, by the residents of a given MGA in comparison with the usage of the subject health care provider by the residents of the other MGAs within the Boundary Region. Operationally, the PRCF 30 is scanned against the list of MGAs in the MGAD 40 and the number of Patient Records or patient discharges per MGA is counted. Thereafter, the counts of patient discharges per MGA are normalized or proportioned in terms of percentages. Step 130 generates a data set or array 132 which is preferably a two dimensional table or array associating each MGA listed in data set 127 with a proportion or percentage quantum.

A fourth step 135 ranks the MGAs listed in data set 132 by order of quantum of proportion and calculates the cumulative proportion of usage associated with the MGAs to generate a data set 137, which is exemplified in FIG. 4. In FIG. 4, forward sorting areas (FSA) of postal codes are used in a fictitious example to represent the MGAs.

A fifth step 140 extracts a list of MGAs from data set 137, the residents of which compose a Pareto efficient level of representation of the patient population, i.e. the actual group of persons frequenting the subject health care provider. It should be appreciated that the subject health care provider typically has patients who live in a wide variety of locales.

Some of these locales, i.e. MGAs, will only have a sparse number of the population thereof attending the subject health care provider. Given the very low attendance or representation of the residents of these locales, they should not be considered as part of the service area which the subject health care provider can be said to efficiently serve. Hence, step 140 ensures that only those locales which have a statistically significant population attending the subject health care provider are considered. This subset of MGAs is stored in data set 142, and it defines the Catchment Area for the subject health care provider.

Figures 4A, 4B:
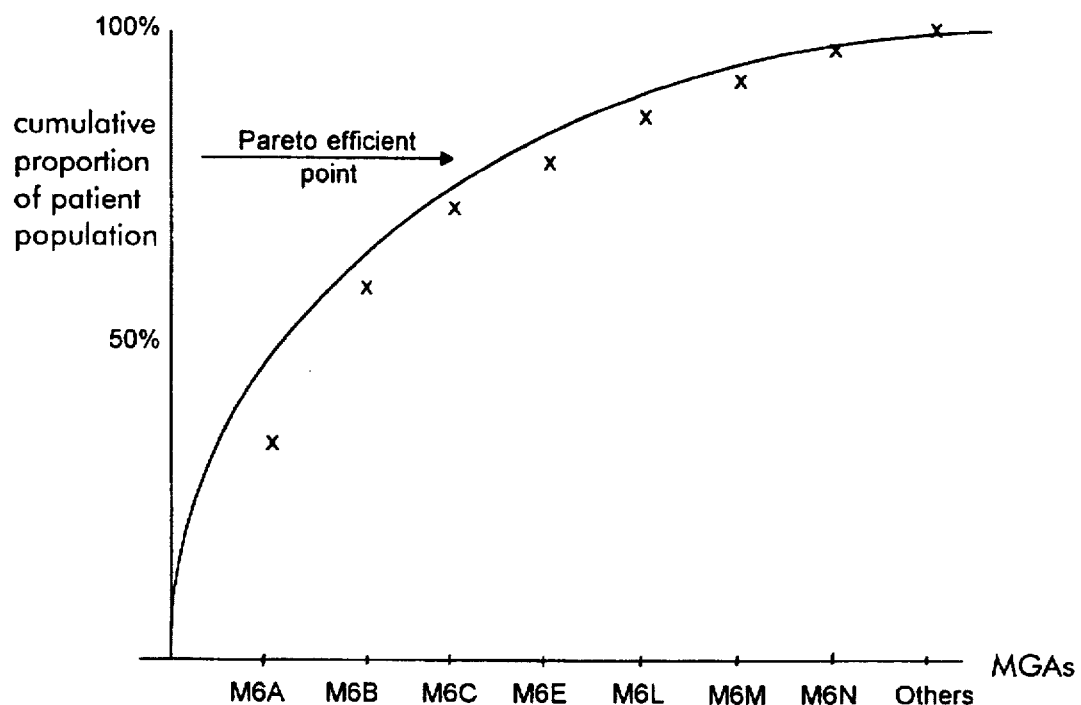
FIG. 4A is a schematic illustration of an electronic data set or array representing an ordered list of Micro-geographical Areas.
FIG. 4B is a graph of Micro-geographical Areas ranked in terms of their respective proportion of a patient population.

The Pareto efficient level is set so as to include a subset of MGAs wherein the residents thereof cumulatively compose approximately 80% of the subject health provider's patient population. However, this is preferably not a fixed value but is subject to change depending on the specific distribution of the patient population throughout the MGAs. FIG. 4B, which is a graph showing cumulative proportion of usage plotted against (ranked) MGAs, exemplifies such a distribution. The boundary or threshold for the Pareto efficient group of MGAs is preferably chosen at the MGA where the curve of cumulative proportion of usage begins to "level off", i.e. where the change in slope is below a threshold level.

A sixth step 145 provides logic for mapping the Catchment Area (defined in data set 142) via output maps 150 and/or terminal display 155.

The procedure described herein for determining the Catchment Area may be applied with respect to the subject health care provider considered as a whole, or for any one or more given Departments thereof, or even specific medical services. In the latter case, the proportion of usage or patient discharges by the residents of the various MGAs is determined only with reference to the subject Department(s) or specific medical service, and a catchment area map can be produced for each Department or medical service. Similarly, module 100 can be executed for a number of health care providers to produce catchment area maps therefor or for any departments thereof.

By using the aforementioned procedure, which is a standardized and technical method for determining catchment areas associated with one or more types of medical services within a boundary region, it is possible to compare the catchment areas and easily visually determine the extent a given health care provider is servicing the surrounding community in respect of a given Department or particular type of medical service.

Determining Referral Population

Another precursor or initialization procedure determines the demographics of a population which generally frequents the subject health care provider, i.e. the Referral Population. This procedure examines each of the unique or distinct MGAs listed in the PRCF 30 to determine, for each segment or population cohort of the MGA, what portion thereof should be considered as part of the Referral Population. It should be appreciated that the demographics of the referral population associated with the subject health care provider can be significantly different from that of the referral population associated with other health care providers situated in the Boundary Region. These differences could affect the accuracy of any projections of demand for medical services. For example, a referral population associated with a first health care provider may have a relatively large middle aged population while a referral population associated with a second health care provider may have a relatively large young adult population. As these populations change over time, the first referral population will begin to demand more geriatric type medical services than the second referral population. Accordingly, by using the invention's "segmented market share" approach, the unique demographics of the Referral Population can be accounted for.

Figure 5:
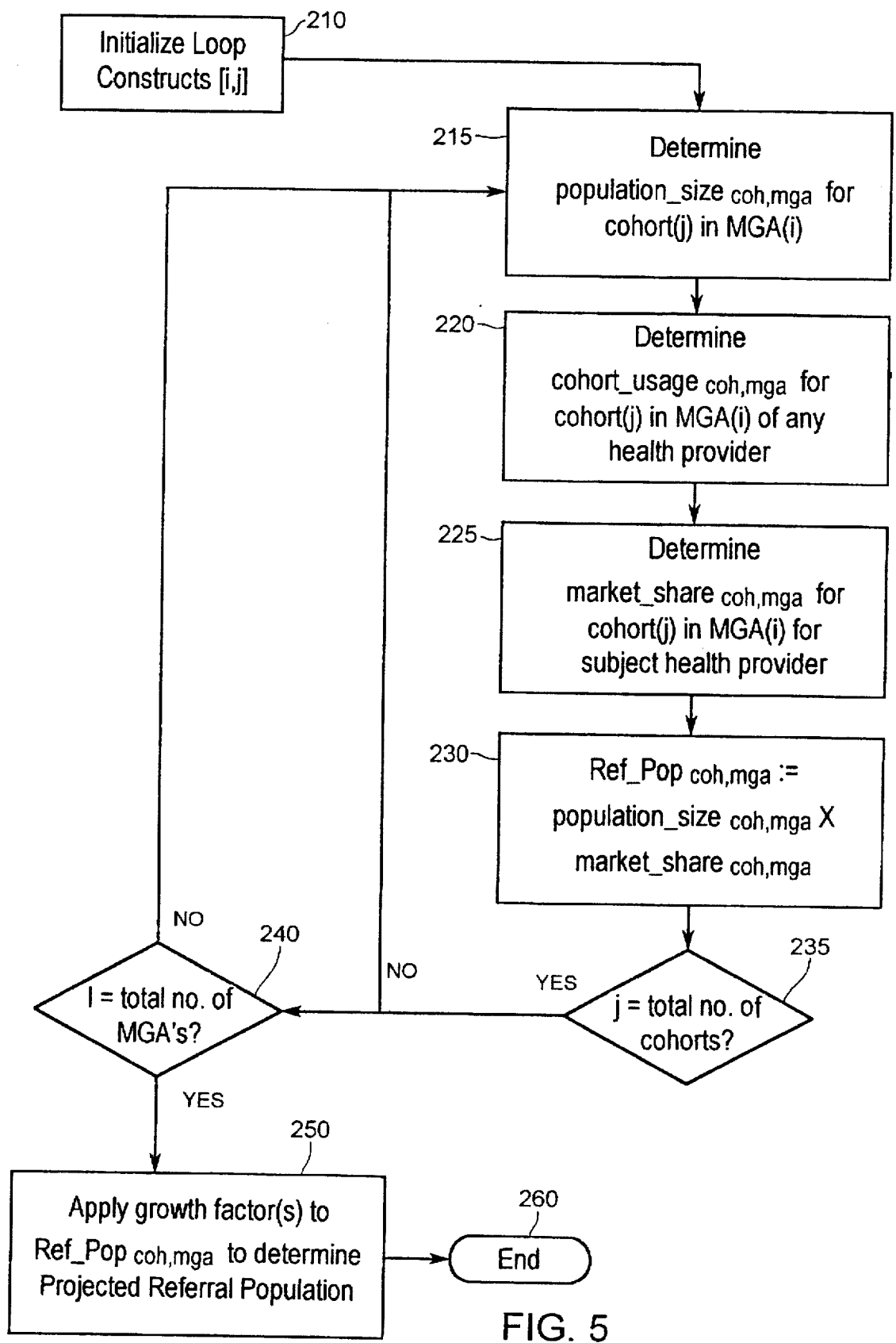
FIG. 5 is a flow diagram of a module which determines a Referral Population for a subject health care provider.

Module 200, which is illustrated in the flow diagram of FIG. 5, establishes the Referral Population for the subject health care provider. A first step 210 initializes control variables for a nested loop construct. A second step 215 examines the census data file 45 (not shown in the flow chart of FIG. 5) and notes the number of people (population_size$_{coh,mga}$) in a specified age group or cohort (cohort$_j$) for a given MGA (MGA$_i$). Preferably, the cohorts are defined by sex in 5 year increments, except for cohorts below and above threshold ages such as 15 and 70 respectively. A third step 220 determines, from the PRCF 30, the number of persons (cohort_usage$_{coh\ mga}$) in the specified cohort for the given MGA who actually attended or frequented any health care provider situated in the Boundary Region. A fourth step 225 calculates the market share (market_share$_{coh,mga}$) for the subject health care provider with respect to the specified cohort, i.e. the number of people in the specified cohort attending the subject health care provider divided by the number of people in the specified cohort attending any health care provider within the Boundary Region (obtained in step 220). A fifth step 230 determines the referral population (Ref_Pop$_{coh,mga}$) for the specified cohort in the given MGA, which is calculated as the total population (obtained from step 215) multiplied by the market share for the specified cohort (obtained from step 225). A sixth step 235 and a seventh step 240 are loop control instructions for ensuring that steps 215—230 are repeated for each defined cohort and each MGA in the Boundary Region.

Steps 210—240 collectively produce a referral population data set or array 245, which is schematically illustrated with fictitious data in FIG. 6. An eighth step 250 applies growth factors, obtained from the growth projection data file 45, to the referral population data set 245 and generates a Projected Referral Population, which is stored in a data set or array 255 schematically illustrated in FIG. 7. The Projected Referral Population represents the demographics of an expected patient population at a specified future year, such as 5 or 10 years forward in time.

The population growth factors are typically obtained from government sources. However, as these growth factors are usually in respect of a large jurisdiction, the system preferably "fine tunes" the growth factors when applying them to a small region such as a given MGA. This fine tuning is preferably accomplished by obtaining data from municipal planning authorities as to how many housing units are proposed to be built over a specified future time frame. If a large number of housing units are scheduled to come on stream in the next few years for the given MGA, the population growth factor therefor is boosted. Conversely, where relatively few housing units are destined to come onstream, or should there be a scheduled contraction in the number of housing units available, the population growth factor for the given MGA is decreased. What constitutes a high or low level of proposed housing units is preferably judged with respect to a threshold value, such as the mean number of housing units destined to come onstream for the collection of MGAs composing the Boundary Region.

A number of methods can be employed to determine the level of variation of the population growth factor from the government or standard figure. It is preferred to correlate, for each MGA, historical variations in housing units from the mean with historical variations in population growth from the officially estimated amount for the jurisdiction wherein a given MGA is situated. The data for this analysis is obtained from historical municipal plans, historical census data (from data file 50), and published government population growth figures. This retrospective view advantageously considers the fact that various neighbourhoods can be largely populated by certain ethnic groups, some of which typically tend to have larger families than others. Of course, such data is not always readily available and in alternative embodiments the population growth factor per MGA can be determined by performing known regression analysis techniques with respect to historical population growth per MGA (from census data file 50). This method, however, does not explicitly consider population growth due to known changes in housing availability.

Demand Module

Figure 8:
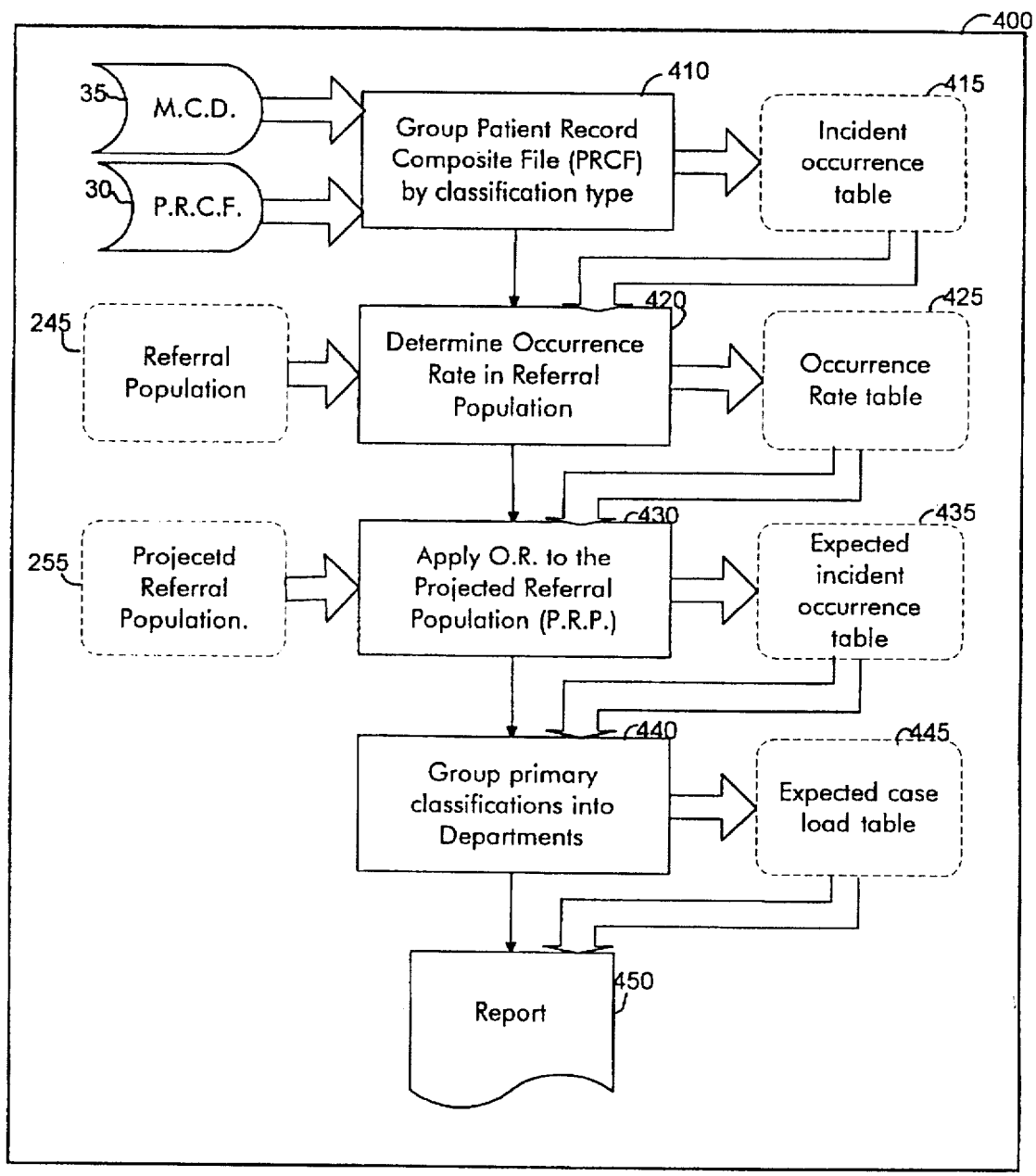
FIG. 8 is a flow diagram of a module which forecasts future case loads for the subject health care provider.

Module 400, shown in the data and process flow diagram of FIG. 8, calculates the expected health resource consumption for the Projected Referral Population. A first step 410 examines the records of the PRCF 30 for those patients living within the Boundary Region and counts, for each cohort, the number of incidents of each type or category of Diagnosis and Medical Procedure listed in the primary classification list of the MCD 35 (which, as mentioned, is preferably the ICD-9 classification system). This information is organized and stored in an incident occurrence data set or table 415, a portion of which is schematically illustrated in FIG. 9 with fictitious occurrence data. The incident occurrence table is preferably generated from Patient Records compiled during the latest full year available in the PRCF 30.

A second step 420 calculates, for each cohort, an occurrence rate (alternatively "O.R.") for each member of the ICD-9 classification system. This rate may be in the form of an equation or a static number. In the latter case, a current occurrence rate for each medical service is computed by dividing the number of occurrences this service was provided to a given cohort by the population size thereof. The results are stored in an O.R. data set or table 425, a corresponding portion of which is schematically illustrated in FIG. 10. For example, from FIG. 6 (which schematically illustrates the Referral Population) it is noted that there are 9,034 males in the 65–69 cohort, and from FIG. 9 the total number of occurrences of cardiac arrest, which is represented by ICD-9 code #4275, is 347 occurrences for this cohort, so the current occurrence rate for this particular malady in respect of the male 65–69 cohort is 3.84%, as shown in FIG. 10.

In the preferred embodiment, the current occurrence rate is used in conjunction with historical data present in the PRCF 30 to derive an occurrence growth rate equation for a select group of medical services. To derive this equation, it is preferred to calculate (static) occurrence rates in respect of each of these medical services for a series of years thereby to generate a plurality of occurrence rate data points. Thereafter, a known regression analysis or "best curve" fitting technique, such as the least squares method and the like, is employed to determine the occurrence rate equation per medical service. It should be appreciated that the occurrence rates for some disease manifestations, such as A.I.D.S. and A.I.D.S. related complications, are growing at alarming rates, so it is desirable to calculate the growth curves thereof in order to accurately forecast the expected occurrence rate therefor. Of course, with over 15,000 ICD-classifications, calculating a growth curve for each one of these is relatively computationally intensive, so the software 25 is preferably constructed to calculate an occurrence rate growth curve for a selected subset of medical services, such as for problematic sexually transmitted diseases and other types of infectious diseases, cancers, etc.

A third step 430 applies the occurrence rate for each medical service, in respect of each cohort, to the Projected Referral Population data set 255. There are two methods by which the occurrence rate can be applied to the Projected Referral Population. A stable rate can be employed using the static current occurrence rates obtained in step 420, or more preferably the occurrence rate growth equations derived in step 420 can be employed to calculate the future occurrence rate. In either case, the occurrence rate table 425 is applied to the Projected Referral Population data set 255 to generate an expected incidence occurrence table 435, a corresponding portion of which is schematically illustrated in FIG. 11 (based on a static rate application).

A fourth step 440 groups the primary classification system, i.e. ICD-9 codes, used in table 435 into the preferred highest level classification system, e.g. Departments, and stores the result in an excepted case load data set or table 445 for reporting purposes. A fifth step 450 generates reports from table 445, one of which is exemplified in FIG. 12. (Note that the example report shown in FIG. 12 does not correspond with the data shown in FIGS. 9–11.)

The above described preferred method for forecasting medical service demand has been found to yield a 96% correlation in practice. Given this very good correlation, it is possible for the subject health care provider to plan for the future by increasing or decreasing the subject health care provider's resources based on the anticipated demand. For example, it may be necessary to expand a Department in terms of equipment and human resources should there be a large anticipated increase in case loads for that Department.

When the subject health care provider is a plurality of hospitals, or has geographically dispersed facilities, it becomes more difficult to know how to geographically allocate health resources. To assist in this task, module 100 allows for the mapping of the Catchment Area, which results in a visual map of the significant MGAs serviced by the facilities and the density of service of each MGA. This mapping will assist the planner in appropriately distributing health resources.

Once the expected case load is predicted, a next step (not shown) in the preferred embodiment is to generate a financial budget forecast. This may be based on a prospective payment system, in which case the expected number of occurrences per ICD-9 code are converted into a DRG or CMG caseload whereupon the budget can be computed. Alternatively, a current cost per case can be computed and this value can be multiplied with the expected caseload to thereby calculate expected costs.

Service Efficiency Module

Figure 13:
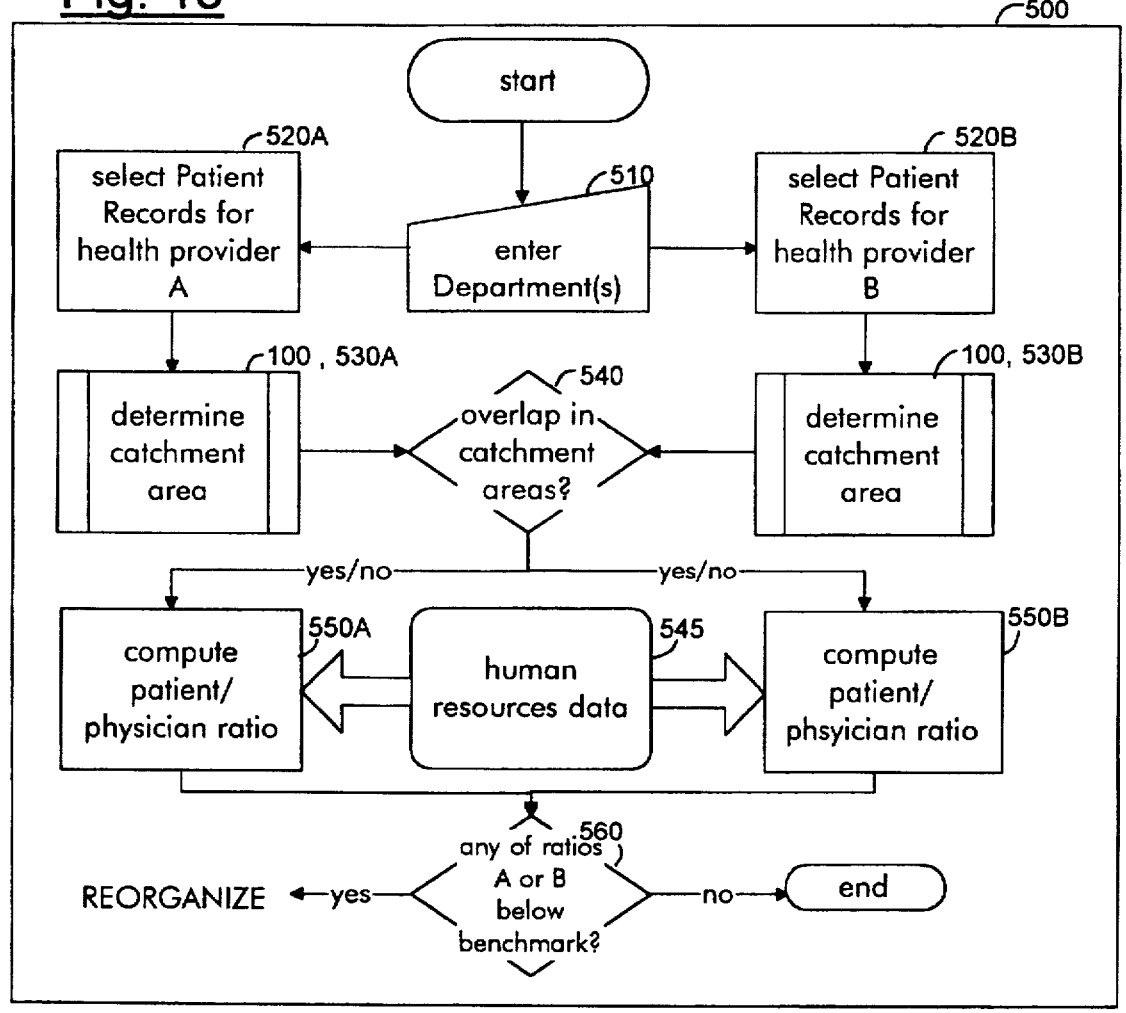
FIG. 13 is a flow diagram of a module which identifies service redundancies and overcapacities amongst various health care providers.

FIG. 13 shows the flowchart for module 500 which computes the service efficiency for two or more health care providers. A first step 510 accepts input relating to which Department(s) are to be analyzed. A second set of steps 520A and 520 B selects the Patient Records associated with the health care providers from the PRCF 30 (not shown in FIG. 13). A third set of steps 530A and 530B computes the respective catchment areas for the health care providers by calling module 100 and supplying it with the Department criteria. A fourth step 540 compares the two catchment areas and determines if there is any geographical overlap therebetween. If there is no overlap, then that implies that it is not possible to procure savings by combining functions and resources of the two Departments because each health care provider is efficient in terms of the area serviced by it. A fifth set of steps 550A and 550B calculates physician/patient ratios for the health care providers. These steps access a human resources data file 545 which details how many physicians and other medical care personnel the subject health care providers require. Finally, a sixth step 560 compares the physician/patient ratios against a benchmark value to confirm whether or not the health care providers are operating efficiently. If both ratios are below the benchmark value, and both catchment areas overlap to some extent, then it may be possible to re-structure the Departments such that one is discontinued and the other is expanded to receive the patients attributable to the former. One the other hand, if only one of the health care providers has a physician/patient ratio below the threshold, then it may be possible to reduce the resources associated with that Department in order to make it more operatively efficient.

This same benchmark process is repeated for other resources including beds, operating rooms, day surgery facilities. By recalculating budget information the potential savings resulting from achieving different benchmarks are calculated. This information about potential savings is key to decision making and the process of running the software for various scenario's marks this system an invaluable tool for health administrators and planners.

The benchmark physician/patient ratio can be a predetermined value programmed into the system, or more preferably it can be dynamically computed by computing the physician/patient ratios for a variety of health care providers within a region, ranking them, and then choosing as the benchmark a value equivalent to a specified percentile thereof, such as a 75% level.

In the preferred embodiment, module 500 can be selectively applied to current data (as reflected in the PRCF 30) or to the future by analyzing the health demand forecast computed by module 400.

Regional Analysis Module

Figure 14:
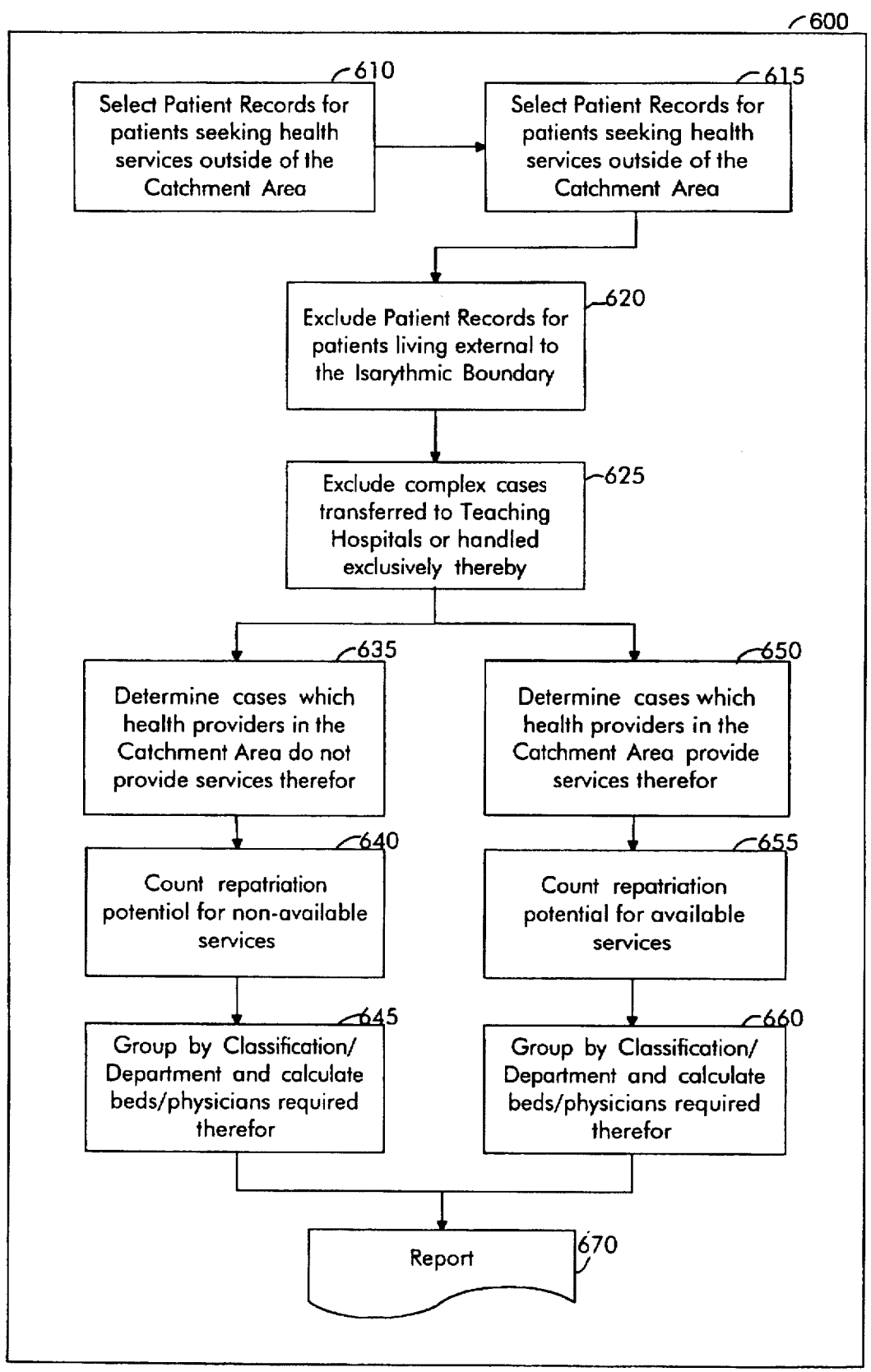
FIG. 14 is a flow diagram of a module which analyzes patient repatriation potential for the subject health care provider.
Figure 16:
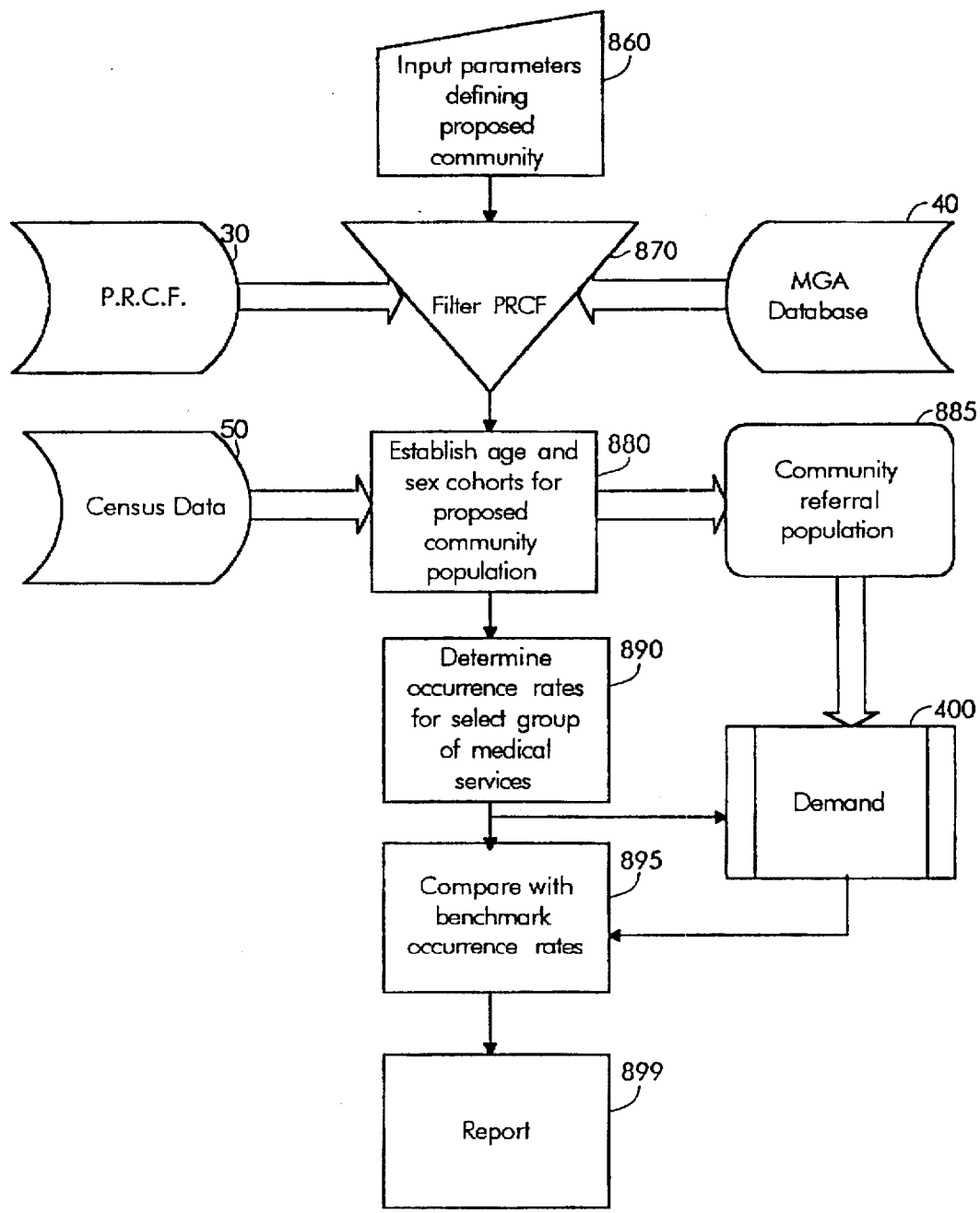
FIG. 16 is a flow diagram of a function which profiles the health care needs of an existing community and highlights any aberrations in existing or forecasted demand in comparison with benchmark levels.

FIG. 14 is a flow diagram for module 600 which determines patient repatriation potential for the subject health care provider in terms of capturable patient market share, i.e. the number of patients frequenting health care providers other than the subject provider within the Boundary Region. A first step 610 seeks scans the PRCF 30 and, with reference to the MGAD 40, selects or notes those Patient Records in respect of patients who seek medical services from health care providers situated external to the Catchment Area. Preferably, the PRCF 30 includes Patient Records for a large area, such as an entire city, and possibly beyond the Boundary Region so that the selection made by step 610 is as complete as possible.

A second step 615 calculates an Isarythmic Boundary, which is a geographical boundary wherein all points within said boundary are geographically closer to the subject health care provider (or the centrex point where the subject health care provider comprises a plurality of geographically situated facilities) than any other health care provider. For the purposes of module 600, step 615 preferably employs commercially available, prior art, geographic software and a geographic database which associates or links each address (found in the Patient Record) with a geographical co-ordinate, so that the Isarythmic Boundary can be accurately calculated.

A third step 620 excludes Patient Records obtained in step 610 which are for patients who live external to the Isarythmic Boundary. The theory is that patients will often choose a health care provider simply because it is the closest to their residence and therefore such patients are less likely to be considered as "repatriatable".

A fourth step 625 excludes Patient Records selected above for patients who have been assigned to tertiary or quaternary care providers due to the complexity of their affliction or for complex cases serviced exclusively by such providers. The theory is that certain illness require particular medical expertise which is likely to be found only at certain hospitals and thus these types of cases should not be considered to be repatriatable. Operationally, step 625 scans the Patient Records selected as a result of steps 610 and 620 for Patient Records wherein treatment for a given patient began with the subject health care provider and continued at the tertiary or quaternary care provider. Preferably the Patient Record as compiled in the PRCF 30 will have a field for noting the transfer of patients. However, if this is not the case it is possible to estimate the number of transfers by matching Patient Records for patients who have attended the subject health care provider and any tertiary or quaternary care provider in respect of the same type of illness, as preferably specified by case management groupings, within a relatively short period of time.

In addition, step 625 scans the Patient Records selected in steps 610 and 620 and excludes "complex cases". A complex case is identified as a medical service belonging to a group of ICD-9 codes which has been found to require treatment by extremely specialized physicians. Preferably, a preselected list of ICD-9 codes representing complex cases is programmed into the system 25.

A fifth set of steps 650 and 635 determine which cases health care providers situated in the Catchment Area provide or do not provide services for. Operationally, this step is preferably accomplished by knowing at the outset what Departments each health care provider in the Catchment Area maintains and simply including or discounting the primary disease and medical procedure classifications associated therewith. Alternatively, the PRCF 30 can be scanned for health care providers situated within the Catchment Area and each unique instance of a member of the primary classification system listed in the PRCF 30 therefor can be considered an available. This list of available services is then compared against the master primary classification list in the MCD 35, and any member thereof not present in the list of available services can be considered as a non-available service.

A sixth set of steps 655 and 640 respectively count the repatriation potential, i.e. the number of Patient Records selected in earlier steps, in terms of those Patient Records associated with available or non-available services. A seventh set of steps 660 and 645 respectively group the primary classification codes employed in the Patient Records selected as a result of steps 655 and 640 into a number of cases per Department. In addition, steps 655 and 640 calculate the extra number of beds and/or physicians required per Department to handle the repatriatable workload. This calculation can be achieved by using benchmark patient/physician ratios per Department, as discussed above with reference to module 500. An eighth step 670 reports the repatriatable workload, preferably in terms of the repatriation potential for available services and non-available services respectively.

Profile Module

Figure 15:
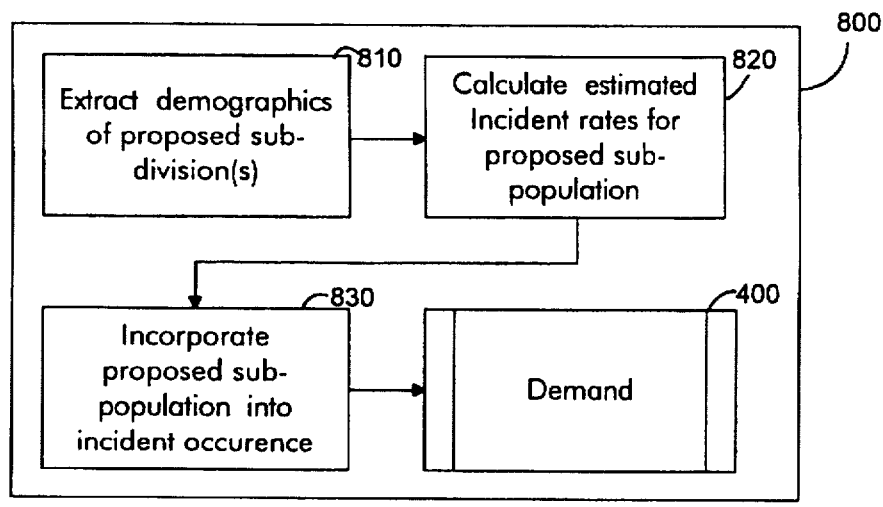
FIG. 15 is a flow diagram of a module which modifies the future case load forecast for the subject health care provider by assessing the impact thereon due to proposed or planned communities.

Module 800, which is shown in the flowchart of FIG. 15, analyzes the impact of proposed new communities or subdivisions upon the forecasted health resource demand for the subject health care provider.

A first step 810 establishes demographics for the proposed subdivision. In the preferred embodiment, a series of sub-steps are employed with respect to each MGA composing the proposed subdivision. A first sub-step scans the growth projection database 45 for municipal planning data to determine the number of housing units planned for the subdivision and the price ranges thereof. This results in a two-dimensional table of price ranges and expected housing units associated therewith. A second sub-step examines historical planning data and historical census data and generates, for each price range, a breakdown of cohort size as well as a breakdown of ethnicity in accordance with the historical data. For example, suppose that 1000 housing units priced under $100,000 are expected to be built in the proposed subdivision. Suppose further that the historical data reveals that 5000 housing units priced under $100,000 were constructed in the previous six years. If 600 males in the 25–29 cohort and 400 males in the 30–34 cohort moved into these housing units, then the former cohort represents 12% of the expected subdivision population (in respect of housing units priced under $100,000) and the latter cohort represents 8% of the population thereof. Similarly, these males can be segmented into defined ethnic categories to thereby compute an ethnic breakdown for these cohorts in the proposed community. A third sub-step multiplies the cohort and ethnicity breakdowns against the scheduled number of housing units to be built (obtained in the first sub-step) for each defined price range to compute the demographics of the proposed sub-division population. For example, the above described 25–29 male cohort for housing units priced under $100,000 will consist of 120 persons (12% of 1000) and the 30–35 male cohort for housing units priced under $100,000 ill consist of 80 persons (8% of 1000).

A second step 820 computes hypothetical occurrence rates for the proposed sub-division population. As discussed before with reference to module 400, these occurrence rates are computed for each type of medical service per cohort, but because there is no actual patient discharge data, it is necessary to use representative occurrence rate values derived from a large population, such as the entire Boundary Region. For example, the occurrence rates for the above described 25–29 male cohort are preferably the medical service occurrence rates calculated for that portion of the entire 25–29 age cohort (in the entire boundary region) who live in housing units priced under $100,000. In addition, step 830 preferably takes into account the ethnicity breakdown per cohort, that is, when computing the occurrence rates per cohort with respect to the general population, only persons of a same, given ethnicity are selected from the general population to determine occurrence rates per ethnicity, per cohort. In this manner, diseases which afflict particular ethnic groups above the norm (such as the affinity of persons of Ashkenazi Jewish heritage for being afflicted with Tay Sachs disease or the relative rarity of coloured persons acquiring skin cancer) can be accounted for. In addition, it has been found that certain ethnic groups have a tendency to use public health care facilities to a much greater extent than other types of ethnic groups and thus this phenomenon can be factored into the occurrence rate calculation.

A third step 830 incorporates the occurrence rates computed in step 820 into the occurrence table 415, and then a fourth step calls and executes portions of the demand module 400. In the preferred embodiment, a system operator can select whether or not to employ the fine tuning of the growth projection factors which normally occurs in module 400. The choice will often depend to a large extent upon the characteristics of the data available, such as whether the MGA wherein the proposed subdivision is located has only recently begun to explode in growth and there is insufficient census data available. It should be noted that with module 800 it is important that the historical planning data be relatively complete but it is not necessary to have extensive historical census data as the demographics of persons moving into recently constructed sub-divisions can be determined from the latest census data available.

An additional aspect of module 800 analyzes the current health status and needs of a particular community in order to identify any particularly demanding health service requirements. In this function of module 800, a first step 860 accepts input identifying the community in terms of the MGAs composing it. A second step 870 queries or filters the PRCF 30 so that only those records corresponding to patients residing in the community are selected.

A third step 880 accesses the census data 50 and segments the total population of the community into pre-selected age and sex cohorts. This results in a Community Referral Population table 885 which, in this case, consists of all persons residing in the community. (A market share approach is not utilized here because the focus here is not a particular subject health provider but the entire community.)

A fourth step 890 computes medical service occurrence rates for the community. In the preferred embodiment, the system computes occurrence rates for only a pre-selected key group of medical services, such as obstetrics or urology. Moreover, for the purposes of this function, the occurrence rates can be calculated in terms of CMG or DRG classification codes.

A fifth step 895 compares the computed occurrence rates with benchmark rates, such as the mean occurrence rates of the key medical services for a wide-ranging area, such as an entire state, city, etc. A sixth step 899 reports on the comparison and highlights medical service requirements which significantly exceed the benchmark levels. In this manner, the foregoing aspect of module 800 provides a profile of the specific needs of the community in comparison with the norm, and can provide indicators, such an unusually high cancer rate, etc., which would alert public health authorities to investigate potential causes for such abnormalities.

The preferred embodiment also utilizes the Community Referral Population table 885 in order to forecast future medical service demand. Profile module 800 executes a portion of demand module 400 (as well as module 200) responsible for computing incident occurrences for projected referral populations. This results in a forecast of the number of incidents expected to occur for the key group of medical services. Step 895 can then compare the forecasted amount with a benchmark amount, such as the mean number of expected key medical service occurrences calculated for a variety of communities. Step 899 reports and highlights any aberrant results.

In describing the preferred embodiment, implicit reference has been made to constructing the software 25 with a database language, such as SQL, but it will be appreciated that the software 25 can be readily constructed from more procedurally orientated languages such as Basic, Pascal etc. Moreover, it will be appreciated by persons skilled in the art that the present invention is not limited by what has been particularly shown and described herein. Rather, the scope of the present invention is defined by the claims which follow.

What is claimed is:

1. A computer-implemented method of optimizing the allocation of health resources for at least one subject health care provider, comprising the steps of:

providing census data and patient discharge records for substantially all of the patient populations of the subject health care provider and other major health care providers within a boundary region, said patient discharge records including an address field indicating one of a plurality of micro-geographical areas (MGAs) where a patient resides, the MGAs for logically apportioning the boundary region into sub-areas having roughly equal population sizes;

establishing a referral population;

calculating occurrence rates of medical services for the referral population;

providing and applying population growth factors to the referral population thereby projecting it to a future time;

applying said occurrence rates to the projected referral population thereby forecasting the consumption of health resources for the subject health care provider; and altering the composition of the health care provider's resources in accordance with said forecast.

2. A method according to claim 1 wherein the step of establishing a referral population comprises the steps of:

determining a market share of the subject health care provider in the boundary region; and selecting portions of the population of the boundary region generally in accordance with said market share thereby establishing the referral population.

3. A method according to claim 2 including the steps of:

providing housing development planning data for a proposed community;

establishing the demographics of the proposed community in accordance with historical data in respect of past housing developments which occurred in an MGA wherein the proposed community is situated;

estimating the number of occurrences of medical services for the proposed community population in accordance with occurrence rates for a general population; and incorporating the estimated number of medical service occurrences with the amount of medical services occurrences calculated for the MGA the proposed community is located in.

4. A method according to claim 2 further including the step of computing a financial budget for the subject health care provider.

5. A method according to claim 2 including the steps of:

determining a population size per cohort from said census data, the cohorts being pre-selected; and computing said market share per cohort.

6. A method according to claim 5 wherein said market share is computed substantially per each unique MGA present in said patient discharge records.

7. A method according to claim 6 including the steps of:
determining a current population size, $S^o_{coh,mga}$, per cohort, per MGA, from said census data;
determining a number, $N_{coh,mga}$, of people attending any health care provider, per cohort, per MGA;
determining a number, $H_{coh,mga}$, of people attending the subject health care provider, per cohort, per MGA; and
setting the referral population size for a given cohort and a given MGA, $R^o_{coh,mga}$, such that $R^o_{coh,mga} = S^o_{coh,mga} * (H_{coh,mga}/N_{coh,mga})$.

8. A method according to claim 7 wherein said population growth factors are computed for a given MGA by employing published growth figures for a political jurisdiction associated with the given MGA and varying the published figure generally in accordance with the number of housing units planned for the given MGA.

9. A method according to claim 7 wherein said population growth factor for a given MGA is derived from a regression analysis of historical population growth for the given MGA.

10. A method according to claim 8 wherein said determination of said population growth factor for a given MGA includes the steps of:
determining a first variation in an amount of recently constructed housing units from a recent mean amount of housing units constructed for MGAs composing the jurisdiction;
determining a second variation in historical population growth rate for the given MGA from a historical published jurisdictional growth rate based on birth, date and migration rates;
correlating said first and second variations;
determining a third variation in the present planned number of housing units from a mean amount of planned housing units for MGAs composing the jurisdiction;
applying the correlation to the third variation to thereby compute a variation in the present published jurisdictional growth rate; and
varying the published jurisdiction growth rate by the fourth variation to thereby compute said population growth factor.

11. A method according to claim 8 wherein said step of projecting said referral population includes the steps of:
computing a projected population size, $S^t_{coh,mga}$, per cohort, per MGA, by applying said growth factor per MGA to $S^o_{coh,mga}$, and
computing a projected referral population size, $R^t_{coh,mga}$, per cohort, per MGA, where $R^t_{coh,mga} = S^t_{coh,mga} * (H_{coh,mga}/N_{coh,mga})$.

12. A method according to claim 2 wherein said occurrence rates are static.

13. A method according to claim 2 wherein said occurrence rates are equations derived from historical patient discharge data.

14. A method according to claim 13 including the steps of:
determining, per category of medical service, a plurality of static occurrence rates for a plurality of generally contiguous years;
computing, per category of medical service, a best curve equation for the occurrence rate plurality.

15. A method according to claim 3 wherein the step of determining demographics for said proposed community includes the steps of:
determining the number of housing units planned for said proposed community and the price ranges thereof from the housing development data;
determining, from historical housing development and census data, a breakdown of cohort proportion for each range of housing prices;
multiplying the cohort breakdown against the planned number of housing units to thereby compute the demographics of said proposed community.

16. A method according to claim 15 including the step of determining, from historical housing development and census data, an ethnic breakdown for each cohort per each range of housing price, and wherein said step of computing occurrence rates from the general population comprises the steps of computing occurrence rates for substantially each ethnicity in the ethnic breakdown per cohort by limiting said general population to the respective ethnic group and thereafter combining the occurrence rates computed per ethnic group to thereby compute the total occurrence rate per cohort.

17. A method according to claim 4 wherein said budget calculating step includes the step of calculating a budget based on a prospective payment system.

18. A method according to claim 4 wherein said budget calculating step includes the step of calculating a budget based on a projection of current cost.

19. A method according to claim 2 including the step of computing a catchment area for the subject health provider and thereby allocating health care resources associated with the subject health care provider in accordance with the geographic scope of the catchment area and the density of service therein.

20. A method according to claim 19 wherein the step of computing a catchment area comprises the steps of:
determining, for each MGA in the boundary region, the proportion of usage of the given health care provider's resources by the population thereof;
ranking said MGAs by proportion of usage;
selecting a subset of said MGAs, the subset consisting of the MGA having the highest proportion of usage quantum and including additional MGAS, in descending order of quantum, until the subset of MGAs collectively represent a specified cumulative proportion of usage, thereby determining a Pareto efficient distribution of the given health care provider's patient population.

21. A computer-implemented process for optimizing the consumption of health resources of at least one subject health care provider, comprising the steps of:
providing i) a master disease and medical services classification database (MCD), ii) a patient record composite file (PRCF) having patient records for substantially all of the subject health care provider's patient population and other major health care providers within a boundary region, said patient record including an address field indicating one of a plurality of micro-geographical areas (MGAs) wherein the patient resides, the MGAs for logically apportioning the boundary region into subareas having roughly equal population sizes, iii) a census data file for at least the boundary region, and iv) population growth factors for the boundary region;
determining, from the census data file, a population per each unique MGA present in the address field of the PRCF;
compiling, from the PRCF, a breakdown of the usage of all health care providers by the residents of each MGA;
computing, from the breakdown and the population size, a market share quantum for the subject health care provider per MGA;
selecting portions of the total population of each MGA in accordance with the market share of the subject health care provider therein, thereby determining a referral population per MGA;

determining, with respect to the MCD, occurrence rates of medical service for the referral population per MGA;

applying the population growth factors to the referral population per MGA thereby projecting it to a future time;

applying said occurrence rates to the projected referral population per MGA thereby forecasting the consumption of health resources for the subject health care provider; and altering the composition of the health care provider's resources in accordance with the forecast.

22. A process according to claim 21 further including the steps of:

providing housing development planning data for a proposed community and providing historical planning data for the MGA(s) the proposed community is located in;

determining a population for the proposed community in accordance with the historical planning data;

estimating the number of occurrences of medical services for the proposed community population in accordance with occurrence rates for a general population; and incorporating the estimated number of medical service occurrences with an actual amount of medical services occurrences for the referral population of the MGA the proposed community is located in.

23. A process according to claim 21 including the step of computing a financial budget for the subject health care provider based upon the forecasted health resource demand.

24. A process according to claim 21 wherein said market share per MGA is additionally determined per cohort and said referral population per MGA is additionally determined per cohort.

25. A process according to claim 21 wherein said occurrence rates are static and based upon data for a latest period in the PRCF.

26. A process according to claim 21 wherein said occurrence rates are equations derived from historical patient discharge data composing the PRCF.

27. A process according to claim 21 including the step of computing a catchment area for the subject health provider and thereby allocating health care resources associated with the subject health care provider in accordance with the geographic scope of the catchment area and the density of service therein.

28. A computer-implemented process for optimizing the allocation of health care resources amongst a plurality of health care providers situated within a boundary region, comprising the steps of:

providing a patient record composite file (PRCF) having patient records for substantially all of the subject health care provider's patient population and other major health care providers within the boundary region, said patient record including an address field indicating one of a plurality micro-geographical areas (MGAs) wherein the patient resides, the MGAs for logically apportioning the boundary region into sub-areas having roughly equal population sizes;

establishing a catchment area for each health care provider;

comparing the geographic scope of the catchment areas;

computing a patient/physician ratio for at least one category of medical service for each health care provider; and redistributing or altering the health resources associated with the health care providers in accordance with said ratios providing the catchment areas at least partially overlap.

29. A process according to claim 28 wherein the step of establishing a catchment area comprises the steps of:

determining, from the patient records in the PRCF, the number of patient discharges per unique MGA, per health care provider; and selecting, for each health care provider, a subset of MGAs having the highest levels of patient discharges such that the subset composes a Pareto efficient geographic distribution of the health care provider's patient population, thereby identifying the catchment area for each health care provider.

30. A process according to claim 29 wherein the step of defining a catchment area for a given health care provider includes the steps of:

determining, for a plurality of MGAs in the boundary region, the proportion of usage of the given health care provider's resources by the populace of each MGA;

ranking said MGA plurality by proportion of usage;

selecting a subset of said MGA plurality, the subset consisting of the MGA having the highest proportion of usage quantum and including additional MGAs, in descending order of quantum, until the subset of MGAs collectively represent a specified cumulative proportion of usage, thereby determining said Pareto efficient distribution of the given health care provider's patient population.

31. A computer-implemented process for optimizing the allocation of health care resources of at least one subject health care provider, comprising the steps of providing a patient record composite file (PRCF) having patient records for substantially all of the subject health care provider's patient population and other major health care providers within the boundary region, said patient record including an address field indicating one of a plurality micro-geographical areas (MGAS) wherein the patient resides, the MGAs for logically apportioning a boundary region into sub-areas having roughly equal population sizes;

establishing a catchment area for the subject health provider;

selecting, from the PRCF, patient records in respect of patients seeking health services outside of the catchment area, thereby forming a set;

calculating an isarythmic boundary for the subject health care provider;

excluding from the set patient records in respect of patients living external to the isarythmic boundary;

excluding from the set patient records in respect of complex cases transferred to specified health care providers; and altering the composition of health resources for the subject health care provider in accordance with categories and amounts of medical service listed in the set.

32. A process according to claim 31 wherein the step of establishing the catchment area comprises the steps of:

determining, from the patient records in the PRCF, the number of patient discharges per unique MGA;

selecting a subset of MGAs having the highest levels of patient discharges such that the subset composes a Pareto efficient geographic distribution of the health care provider's patient population, thereby establishing the catchment area.

* * * * *